(12) United States Patent
Moutard et al.

(10) Patent No.: US 9,822,083 B2
(45) Date of Patent: Nov. 21, 2017

(54) AMPHIPHILIC DERIVATIVES OF TRIAZAMACROCYCLIC COMPOUNDS, PRODUCTS AND COMPOSITIONS INCLUDING SAME, AND SYNTHESIS METHODS AND USES THEREOF

(71) Applicant: BIOCELLCHALLENGE, Signes (FR)

(72) Inventors: Stéphane Moutard, Marseilles (FR); Vincent Delauzun, Toulon (FR); Laurent Meunier, Marseilles (FR)

(73) Assignee: BIOCELLCHALLENGE, Signes (FR)

( * ) Notice: Subject to any disclaimer, the term of this patent is extended or adjusted under 35 U.S.C. 154(b) by 0 days.

(21) Appl. No.: 14/762,101

(22) PCT Filed: Jan. 21, 2014

(86) PCT No.: PCT/FR2014/000013
§ 371 (c)(1),
(2) Date: Jul. 20, 2015

(87) PCT Pub. No.: WO2014/111639
PCT Pub. Date: Jul. 24, 2014

(65) Prior Publication Data
US 2015/0353514 A1    Dec. 10, 2015

(30) Foreign Application Priority Data

Jan. 21, 2013 (FR) .................... 13 00125

(51) Int. Cl.
| | | |
|---|---|---|
| *C07D 255/02* | (2006.01) | |
| *A61K 47/22* | (2006.01) | |
| *C07K 16/06* | (2006.01) | |
| *C07K 16/18* | (2006.01) | |
| *C07K 16/32* | (2006.01) | |
| *A61K 47/18* | (2017.01) | |
| *A61K 9/127* | (2006.01) | |
| *A61K 39/00* | (2006.01) | |

(52) U.S. Cl.
CPC .......... *C07D 255/02* (2013.01); *A61K 9/1272* (2013.01); *A61K 47/186* (2013.01); *A61K 47/22* (2013.01); *C07K 16/06* (2013.01); *C07K 16/18* (2013.01); *C07K 16/32* (2013.01); *A61K 2039/505* (2013.01); *C07K 2317/21* (2013.01)

(58) Field of Classification Search
CPC .................................................. C07D 255/02
See application file for complete search history.

(56) References Cited

U.S. PATENT DOCUMENTS 6,180,784 B1    1/2001 Wolff et al.

FOREIGN PATENT DOCUMENTS

| WO | 01/42200 A1 | 6/2001 |
| WO | 01/57064 A2 | 8/2001 |
| WO | 2009/129385 A1 | 10/2009 |

OTHER PUBLICATIONS

Wang et al. (Bioorganic & Medicinal Chemistry Letters (2014), 24(7), 1771-1775).*
International Search Report dated Apr. 1, 2014, issued in counterpart application No. PCT/FR2014/000013 (3 pages).
Zhang, et al., "TACN—containing cationic lipids with ester bond: Preparation and application in gene delivery", Bioorganic & Medicinal Chemistry Letters, Sep. 23, 2011, vol. 21, No. 23, pp. 7045-7049.
Office Action dated Mar. 10, 2017 in co-pending U.S. Appl. No. 15/297,529; without returned SB08; in English (7 pages).
Office Action dated Jun. 26, 2017 in co-pending continuation-in-part U.S. Appl. No. 15/297,529; with PTO892; without returned SB08 (in English; 15 pages).
Nichols et al., "Nanotechnology for Cancer Treatment: Possibilities and Limitations", Ch. 2 in Bae et al. (eds.), "Cancer Targeted Drug Delivery: An Ellusive Dream", Springer Science+Business Media, New York, pp. 37-56 (2013)(in English; cited in the Office Action dated Jun. 26, 2017 in co-pending parent U.S. Appl. No. 15/297,529).

\* cited by examiner

*Primary Examiner* — Bruck Kifle
(74) *Attorney, Agent, or Firm* — Westerman, Hattori, Daniels & Adrian, LLP

(57) ABSTRACT

The invention relates to amphiphilic derivatives of a triazamacrocyclic compound, as well as to said derivatives as active molecule transporters. The invention also relates to a nanodrug including at least one amphiphilic derivative of a triazamacrocyclic compound and at least one active molecule of a protein such as an antibody, in particular for the treatment of autoimmune diseases or for the treatment of cancer.

7 Claims, 11 Drawing Sheets

AMPHIPHILIC DERIVATIVES OF TRIAZAMACROCYCLIC COMPOUNDS, PRODUCTS AND COMPOSITIONS INCLUDING SAME, AND SYNTHESIS METHODS AND USES THEREOF

This invention relates to a new family of lipids in the field of drug chemistry. More specifically, the invention relates to amphiphilic derivatives of triazamacrocyclic compounds for the intracellular transport of molecules of therapeutic interest, in particular for intracellular delivery of antibodies.

There is currently a high demand for systems for intracellular delivery of molecules having a therapeutic potential. The sequencing of the genome and the very rapid development of genomics since the mid-1990s has led to the discovery and development of a very large number of delivery systems dedicated to nucleic acids. However, there are still only few studies on the research and discovery of intracellular delivery systems adapted to other types of potentially therapeutic molecules and in particular antibodies.

Unlike intracellular delivery of genes, for which numerous viral approaches exceed the biochemical or physical approaches for delivering a transgene into a cell and integrating it into its gene pool, the transport of other types of molecules can be performed only with physical and biochemical approaches.

The physical approaches involve, for example, techniques of electroporation, microinjection or sonoporation. They make it possible to deliver nucleic acids or other types of molecules to the interior of cells. These techniques are used more or less successfully in vitro and in most cases are difficult to apply in vivo.

In the context of a biochemical approach, cationic lipids and cationic polymers are used, inter alia, as carriers. The most effective molecules comprise numerous positive charges, which interact electrostatically with the nucleic acids, comprising numerous negative charges.

The complexes formed between the nucleic acids and cationic molecules are:

polyplexes when the complexes are formed with a cationic polymer, or lipoplexes when the complexes are formed with a cationic lipid.

In the case of lipoplexes, the nucleic acids are encapsulated in vesicular structures called liposomes.

The lipoplexes or polyplexes interact with the cell membranes, then deliver their contents to the interior of the cells according to the mechanisms specific to them. However, even if this approach is rather effective for delivery nucleic acids into the cell, at least in vitro, in consideration of the clearly determined physicochemical characteristics of the nucleic acids, the same is not at all true for other types of molecules. For example, if the global negative charge of the nucleic acids enables complexing with cationic carriers, the complexing of proteins with such carriers is much less certain. In this approach, it appears that encapsulation of the molecule to be transported into liposomes is the most suitable. At present, liposomes are the tools most often used for intracellular delivery of therapeutic molecules or genes. Hydrophilic or lipophilic molecules may be encapsulated in these liposomes. These liposomes may consist of a plurality of lipids but, in most formulations currently used, they contain at least one cationic lipid. The cationic lipid is generally associated with a neutral co-lipid such as DOPE (1,2-dioleoyl-sn-glycero-3-phosphoethanolamine). Thus a very large number of cationic lipids have been developed, generally for the transport of genes into the cells.

The first lipid developed for the transport of genes into the cells is DOTMA, as reported in the publication Felgner et al., Proc. Nat. Acad. Sci. 84, 7413 (1987). DOTMA corresponds to N-(1-(2,3-dioleyloxyl)propyl)-N,N,N-trimethyl-ammonium chloride.

The chemical formula of DOTMA is provided below

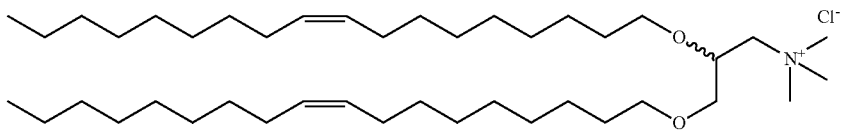 [SMILES: CCCCCCCC/C=C\CCCCCCCCOCC(C[N+](C)(C)C)OCCCCCCCC/C=C\CCCCCCCC ; [Cl-]]

Other molecules have also been developed, ranging from relatively simple structures such as DOTAP (1,2-dioleoyl-3-trimethylammonium-propane) of formula:

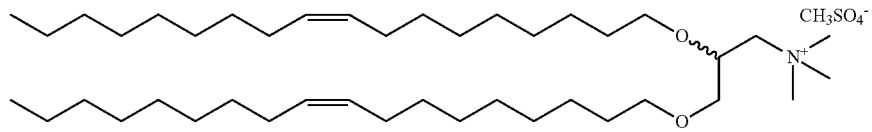 [SMILES: CCCCCCCC/C=C\CCCCCCCCOCC(C[N+](C)(C)C)OCCCCCCCC/C=C\CCCCCCCC ; "CH3SO4-"]

or DMRIE (1,2-dimyristoyl Rosenthal Inhibitor Ether) of formula:

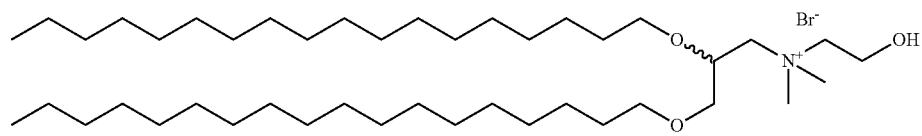 [SMILES: CCCCCCCCCCCCCCCCCCOCC(C[N+](C)(C)CCO)OCCCCCCCCCCCCCCCCCC ; [Br-]]

Molecules with relatively complex or even much more complex structures have also been developed. These include, for example, DOGS (dioctadecylamidoglycyl permine) of formula:

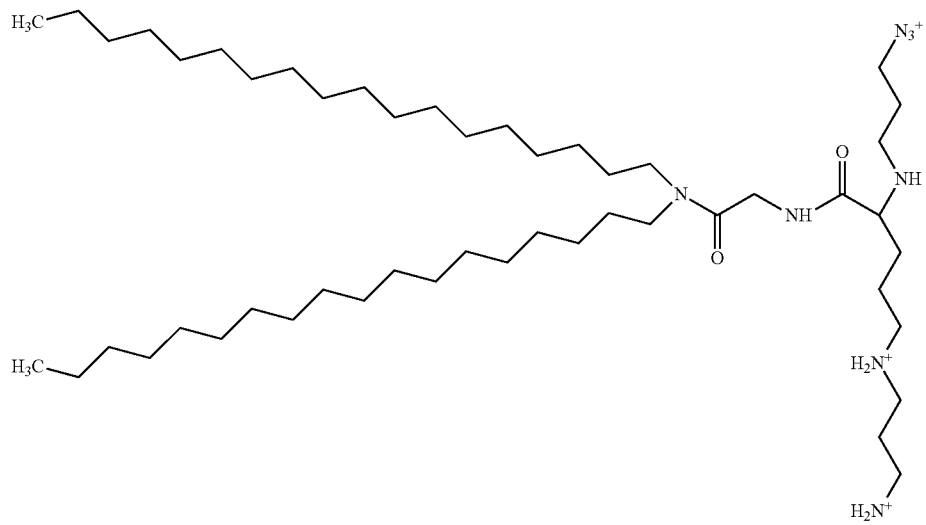

or analogous lipid membranes of d¹ archaebacteria:

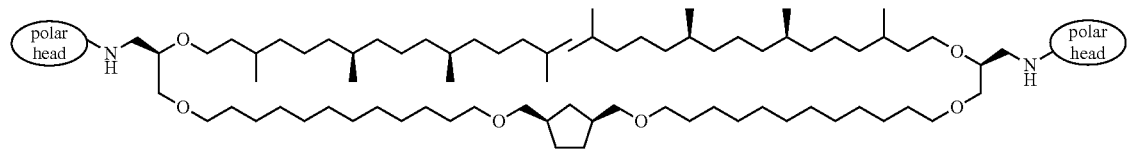

However, the lipid molecules above have been selected and studied for their capacities to transport nucleic acids into the cells for gene therapy purposes. Certain synthesized molecules have then been used to deliver, into the cells, molecules other than nucleic acids such as proteins. However, these systems have been found to be ineffective and unreliable until now.

With regard to the transport of proteins into the cells, scientists generally use sophisticated, time-consuming and expensive methods that are limited in terms of applications. The most studied approach involves using a special class of peptides called protein transduction domains (PTD).

The mechanism of action of the PTDs is not defined at present, and their delivery efficacy varies according to the protein transported. Moreover, one of the major disadvantages concerning the use of these PTDs is the need to chemically couple them to the protein to be transported in order to use them.

There is, at present, a need to develop new carriers or vectors capable of effectively and reliably transporting molecules that are not only nucleic acids, such as, for example, proteins. Such carriers or vectors should ideally make it possible to implement simple, quick and inexpensive methods. They should also be capable of having a wide spectrum of applications.

The solution to the stated problem involves an amphiphilic derivative of a triazamacrocyclic compound of formula (I):

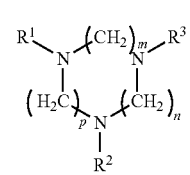   (I)

wherein:
R¹ responds to formula (II):

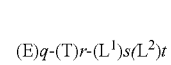   (II)

$(E)q\text{-}(T)r\text{-}(L^1)s(L^2)t$ and wherein:
E represents a linear or branched, saturated or unsaturated hydrocarbon group including 1 to 15 carbon atoms and optionally comprising one or more heteroatoms chosen from nitrogen, oxygen, sulfur, fluorine, chlorine, bromine or iodine;
T represents a branched, saturated or unsaturated hydrocarbon group including 1 to 15 carbon atoms and optionally comprising one or more heteroatoms chosen from nitrogen, oxygen, sulfur, fluorine, chlorine, bromine or iodine;
$L^1$ and $L^2$, identical or different, represent a linear, branched and/or cyclic, saturated or unsaturated hydrocarbon group, including 6 to 24 carbon atoms and optionally comprising one or more heteroatoms chosen from nitrogen, oxygen, sulfur, fluorine, chlorine, bromine or iodine;

q is an integer equal to 0 or 1;

r is an integer equal to 0 or 1;

s and t, identical or different, are integers equal to 0 or 1, on the condition that at least one of said integers is different from 0;

$R^2$ represents a hydrogen atom or a linear, branched and/or cyclic, saturated or unsaturated group, including 1 to 20 carbon atoms, comprising one or more heteroatoms chosen from nitrogen, oxygen, sulfur, fluorine, chlorine, bromine or iodine; and having at least one functional cationic group;

$R^3$ represents a hydrogen atom or is identical to $R^1$, or is identical to $R^2$.

m, n and p, identical or different, are integers equal to 0, 1, 2, 3 or 4.

Surprisingly, the applicant was able to demonstrate, as is reported in the examples, that the amphiphilic derivatives according to the invention re easy to synthesize and enable the effective transport of active molecules or proteins such as antibodies, even preserved in the presence of bovine serum albumin. In addition, the applicant was able to demonstrate that the amphiphilic derivatives according to the invention are effective in different cell types.

This invention also relates, secondly, to the use of a derivative according to the invention as an intracellular carrier of active molecules.

It relates thirdly to a pharmaceutical composition containing at least one derivative according to the invention and a pharmaceutically acceptable carrier.

It relates fourthly to a nanodrug containing, on the one hand, derivatives as described above and, on the other hand, at least one active molecule, i.e. of therapeutic interest.

A nanodrug may be defined as a carrier or vector of nanometric size capable of carrying an active molecule to a given therapeutic target: a gene, a protein, a cell, a tissue or an organ.

The invention also relates, fifthly, to a nanodrug for use in the treatment of autoimmune diseases, cancers, neurodegenerative conditions, certain infectious diseases or genetic diseases causing a specific dysfunction in the body.

It also relates, sixthly, to a product containing a nanodrug according to the invention and at least one second active compound such as a combination product for simultaneous, separated or sequential use for the transport of active molecules of therapeutic interest, in particular for the intracellular delivery of antibodies.

Finally, it relates to a method for synthesis of the derivatives according to the invention.

The different compounds described above may in particular be synthesized according to the methods described in example 1 below, which describe the synthesis of cationic lipids based on TACN (triazacyclononane) making it possible to deliver proteins and in particular antibodies into living cells.

Among the other envisageable applications, the use of the derivatives according to the invention also makes it possible to study the function of the transported molecules or to inhibit or induce an intracellular function in the living cells. As an example, the transport of monoclonal antibodies into the cells may be used to specifically inhibit an intracellular target. This approach has already been demonstrated via the transfection of DNA coding for antibodies called "intrabodies". Similarly, by using the derivatives according to the invention, it becomes possible to use therapeutic antibodies inside the cells even though, until now, the therapeutic antibodies have all had targets outside living cells.

The invention will be easier to understand in view of the following non-limiting description, in view of the appended drawings, wherein.

Figure 1:
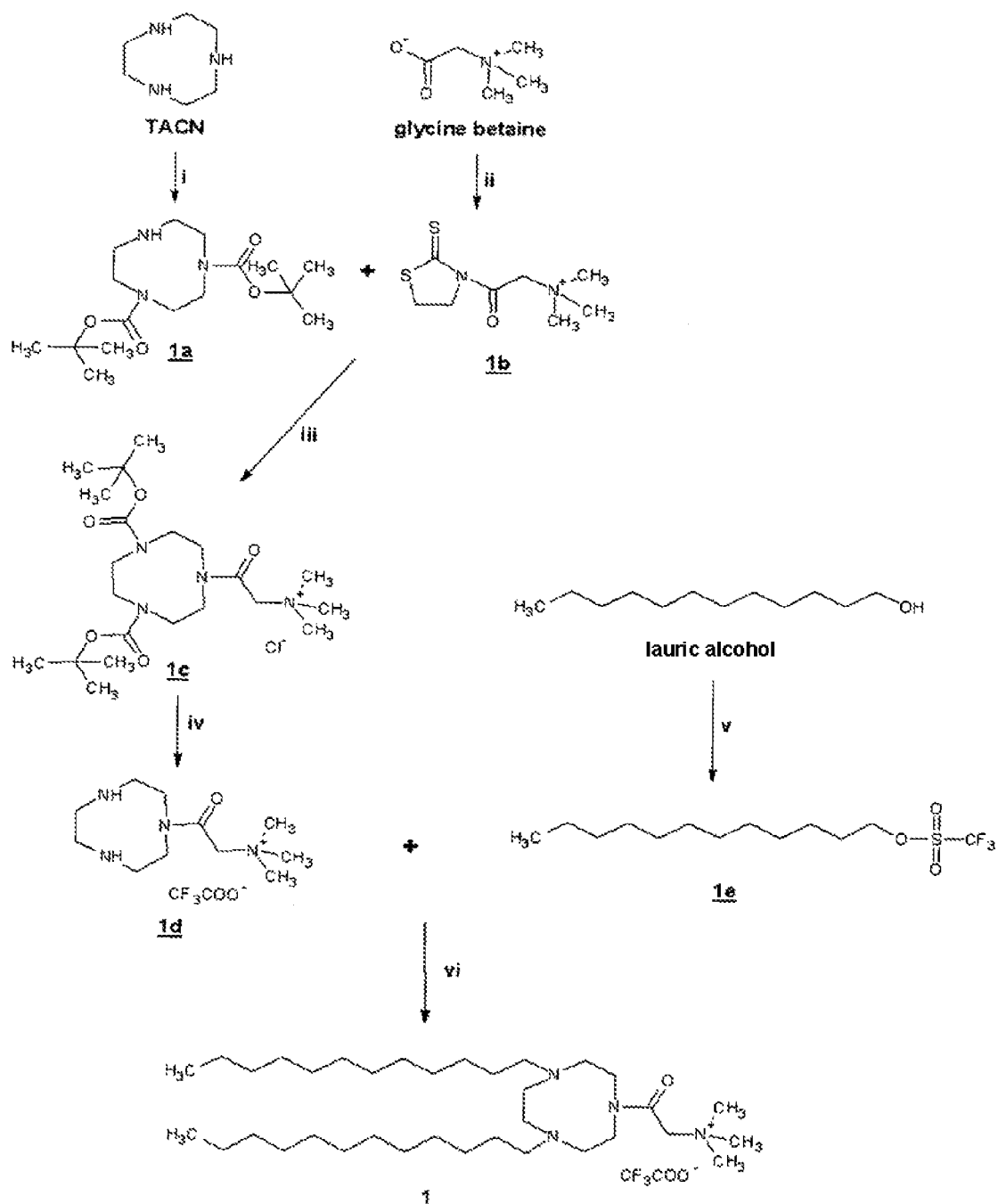
FIG. 1 shows the reaction scheme for the synthesis of 1,4-didodecyl-7-betainyl-1,4,7-triazacyclononane.

The compounds according to the invention are amphiphilic derivatives of triazamacrocyclic compounds of formula (I):

$$R^1\diagdown N\diagup(CH_2)_m\diagdown N\diagup R^3 \atop (H_2C)_p\diagdown N\diagup(CH_2)_n \atop R^2 \qquad (I)$$

wherein:

$R^1$ responds to formula (II):

$$(E)q-(T)r-(L^1)s(L^2)t \qquad (II)$$

and wherein:

E represents a hydrocarbon, linear or branched, saturated or unsaturated group including 1 to 15 carbon atoms and optionally comprising one or more heteroatoms chosen from nitrogen, oxygen, sulfur, fluorine, chlorine, bromine or iodine;

T represents a branched, saturated or unsaturated hydrocarbon group, including 1 to 15 carbon atoms and optionally comprising one or more heteroatoms chosen from nitrogen, oxygen, sulfur, fluorine, chlorine, bromine or iodine;

$L^1$ and $L^2$, identical or different, represent a linear, branched and/or cyclic, saturated or unsaturated hydrocarbon group, including 6 to 24 carbon atoms and optionally comprising one or more heteroatoms chosen from nitrogen, oxygen, sulfur, fluorine, chlorine, bromine or iodine;

q is an integer equal to 0 or 1;

r is an integer equal to 0 or 1;

s and t, identical or different, are integers equal to 0 or 1, on the condition that at least one of said integers is different from 0;

$R^2$ represents a hydrogen atom or a linear, branched and/or cyclic, saturated or unsaturated hydrocarbon group, including 1 to 20 carbon atoms, comprising one or more heteroatoms chosen from nitrogen, oxygen, sulfur, fluorine, chlorine, bromine or iodine; and having at least one cationic functional group;

$R^3$ represents a hydrogen atom or is identical to $R^1$, or is identical to $R^2$.

m, n and p, identical or different, are integers equal to 0, 1, 2, 3 or 4.

Above and below, by "heteroatom" we mean an atom chosen from nitrogen, oxygen, sulfur and halogens such as fluorine, chlorine, bromine or iodine. By "azamacrocyle" we mean a cyclic macromolecule containing one or more nitrogen atoms as represented in formula (I).

Preferably, in formula (II):

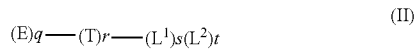
(II)

E, which serves as a spacer arm, responds to the following formula (III):

(III)

wherein:

X represents an alkylene group forming a bridge and including 1 to 8 carbon atoms;

G1 represents a —CO—, —O—, —S—, —NH— or —NR— group wherein R is an alkyl group, advantageously in $C_1$ to $C_6$.

Also preferably, X represents an alkylene group forming a bridge and including 1, 2, 3 or 4 carbon atoms. Still more preferably, X represents an alkylene group forming a bridge and including just 1 carbon atom.

Preferably, in formula (I):

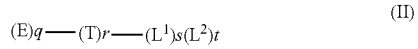
(II)

T, which serves as a branched spacer arm, represents either the residue of an amino acid or the residue of a glycerol.

By "residue of an amino acid" we mean the atom group that subsists from said amino acid when it is covalently bound:
to the spacer arm E in formula (II) or directly to one of the nitrogen atoms of the azamacrocycle in formula (I), and
to one and/or the other of groups $L^1$ and $L^2$ in formula (II).

By "residue of a glycerol" we mean the atom group that subsists from said glycerol when it is covalently bound:
to the spacer arm E in formula (II) or directly to one of the nitrogen atoms of the azamacrocycle in formula (I), and
to one and/or the other of groups $L^1$ and $L^2$ in formula (II).

Preferably, when T represents the residue of an amino acid in formula (II), T is chosen from the twenty amino acids that are classically involved in the constitution of proteins, namely aspartic acid, glutamic acid, alanine, arginine, asparagine, cysteine, glutamine, glycine, histidine, isoleucine, leucine, lysine, methionine, phenylalanine, proline, serine, threonine, tyrosine, tryptophan and valine.

Also preferably, it is chosen from aspartic acid, glutamic acid, leucine, isoleucine and lysine, aspartic acid and glutamic acid.

Alternatively, this amino acid may be chosen from rarer amino acids such as, for example, β-alanine, γ-aminobutyric acid, α-aminoadipic acid, hydroxylysine, α,ϵ-diaminopimelic acid, α,β diaminopropionic acid, α,γ-diaminobutyric acid and ornithine.

Generally, any amino acid may be suitable insofar as the amino acids comprise, by definition, at least two function groups, one carboxylic acid, the other amine, allowing covalent bonding thereof:
to the spacer arm E in formula (II) or directly to one of the nitrogen atoms of the azamacrocycle in formula (I), and
to one and/or the other of the $L^1$ and $L^2$ in formula (II).

Also preferably, T is the residue of an amino acid belonging to series L. It is, however, possible for T to be the residue of an amino acid of series D.

Preferably, in formula (II):

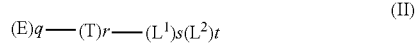
(II)

$L^1$ and/or $L^2$ respond to the following formula (IV):

(IV)

wherein:

$G_2$ represents a —CO—, —O—, —S—, —NH— or —NR— group, in which R is an alkyl group, advantageously in $C_1$ to $C_6$, and Y represents a linear saturated or unsaturated alkyl chain in $C_8$ to $C_{24}$. Y may also represent a cyclic or polycyclic group known for being lipophilic, such as a steroid group, for example derived from cholesterol, a polyaromatic group, for example derived from naphthalene, dansyl, anthracene or a group derived from alkaloids.

Also preferably, Y represents a linear saturated or unsaturated alkyl chain in $C_{12}$ to $C_{18}$.

More preferably still, the derivative of formula (I) according to the invention is such that:

$R^1$ responds to formula (II):

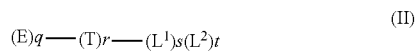
(II)

wherein:
E responds to the following formula (III):

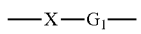
(III)

wherein:
X represents an alkylene group forming a bridge and including 1 to 8 carbon atoms;
G1 represents a —CO—, —O—, —S—, —NH— or —NR— group wherein R is an alkyl group in $C_1$ to $C_6$;
T represents either the residue of an amino acid or the residue of a glycerol;
$L^1$ and/or $L^2$ respond to the following formula (IV):

(IV)

wherein:
$G_2$ represents a —CO—, —O—, —S—, —NH— or —NR— group, wherein R is an alkyl group in $C_1$ to $C_6$, and
Y represents a linear, saturated or unsaturated alkyl chain in $C_8$ to $C_{24}$ or a cyclic or polycyclic group.

Among the triazamacrocyclic compounds according to the invention, those in which the spacer arm E is bound by an amide bond or an ester bond to the branched spacer arm T are preferred, T being itself bound by an amide bond or an ester bond to group(s) $L^1$ and/or $L^2$. This is for reasons of ease of preparation.

In this case, E responds, preferably, to formulas —X—CO— or —X—NH— in which X has the same meaning as above. $L^1$ and/or $L^2$ respond, preferably, to formulas —O—Y, —CO—Y or —NH—Y in which Y has the same meaning as above.

In this case as well it is preferable for $R^1$ to respond to formula (V):

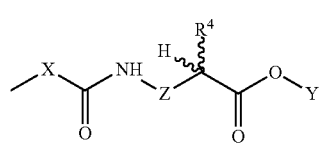
(V)

wherein:
X and Y have the same meaning as above
Z represents:
 either a covalent bond, in which case $R^4$ represents a hydrogen atom, a methyl group, the side chain of an amino acid, or a group of formula (VI):

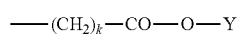
(VI)

wherein k is 1 or 2, and Y has the same meaning as above, or a hydrocarbon group forming a bridge, including 1, 2, 3 or 4 carbon atoms, and capable of comprising one or more heteroatoms chosen from O and N, in which case $R^4$ represents a primary amine group or a group of formula (VII):

(VII)

wherein Y has the same meaning as above.

Also preferably, the derivative of formula (I) according to the invention is such that:
$R^1$ responds to the formula (V):

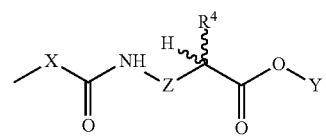
(V)

wherein:
X represents an alkylene group forming a bridge and including 1, 2, 3 or 4 carbon atoms;
Y represents a linear, saturated or unsaturated alkyl chain in $C_{12}$ to $C_{18}$;
Z represents:
 either a covalent bond, in which case $R^4$ represents a hydrogen atom, a methyl group, the side chain of an amino acid, or a group of formula (VI):

(VI)

wherein k is 1 or 2, and Y represents a linear, saturated or unsaturated alkyl chain in $C_{12}$ to $C_{18}$,
or a hydrocarbon group forming a bridge, including 1 to 4 carbon atoms, and capable of comprising one or more heteroatoms chosen from O and N, in which case $R^4$ represents a primary amine group or a group of formula (VII):

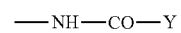
(VII)

wherein Y represents a linear, saturated or unsaturated alkyl chain in $C_{12}$ to $C_{18}$;
$R^2$ represents a hydrogen atom or a linear, branched and/or cyclic, saturated or unsaturated hydrocarbon group, including 1 to 20 carbon atoms, comprising one or more heteroatoms chosen from nitrogen, oxygen, sulfur, fluorine, chlorine, bromine or iodine; and having at least one cationic functional group; and
$R^3$ represents a hydrogen atom or is identical to $R^1$, or is identical to $R^2$.

Advantageously, when T represents, in formula (II):

(II)

the residue of an amino acid chosen from aspartic acid and glutamic acid, then, in formula (V):

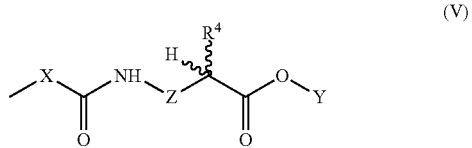
(V)

Z represents a covalent bond;
Y represents, preferably, a linear, saturated or unsaturated alkyl chain in $C_8$ to $C_{18}$ and, better yet, in $C_{12}$ to $C_{18}$;
R5 represents a group of formula (VI): —$(CH_2)_k$—CO—O—Y, wherein k is equal to 1 or 2, and Y represents, preferably, a linear, saturated or unsaturated alkyl chain in $C_8$ to $C_{18}$ and, better yet, in $C_{12}$ to $C_{18}$.

According to yet another preferred provision of the invention, in formula (I):

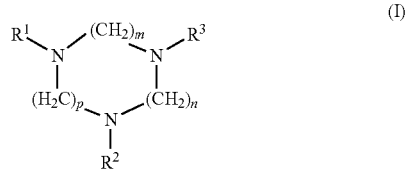
(I)

$R^2$ represents a hydrogen atom or the residue of a cationic amino acid. In the latter case, by "residue of a cationic amino acid" we mean the group of atoms that subsists from an amino acid having at least one cationic functional group when it is covalently bound to one of the nitrogen atoms of the azamacrocycle in formula (I). Preferably, the cationic functional group(s) borne by this cationic amino acid are amino, guanidino, imidazole or quaternary ammonium. In particular, they are chosen from ornithine, lysine, arginine and glycine betaine, glycine betaine being especially preferred.

In formula (I), $R^2$ represents, preferably, a hydrogen atom.

According to yet another preferred provision of the invention, in formula (I), $R^3$ more specifically represents a hydrogen atom plus.

Preferably, the compounds according to the invention are amphiphilic derivatives of triazamacrocyclic compounds for which m, n and p are integers equal to 2. Said preferred derivatives are triazacyclononane derivatives, which satisfy formula (VIII):

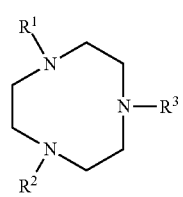
(VIII)

wherein $R^1$, $R^2$ and $R^3$ are as defined above.

Still more specifically, the preferred derivatives responding to formula (VIII) are such that:

$R^1$ responds to formula (V):

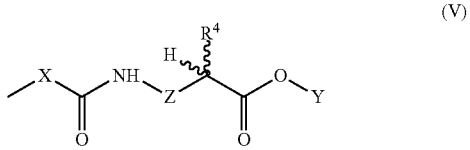
(V)

wherein:
X represents an alkylene group forming a bridge and including 1, 2, 3 or 4 carbon atoms;
Y represents a linear, saturated or unsaturated alkyl chain in $C_{12}$ to $C_{18}$;
Z represents:
  either a covalent bond, in which case $R^4$ represents a hydrogen atom, a methyl group, the side chain of an amino acid, or a group of formula (VI):

—$(CH_2)_k$—CO—O—Y (VI)

wherein k is 1 or 2, and Y represents a linear, saturated or unsaturated alkyl chain in $C_{12}$ to $C_{18}$,
  or a hydrocarbon group forming a bridge, including 1 to 4 carbon atoms, and capable of comprising one or more heteroatoms chosen from O and N, in which case $R^4$ represents a primary amine group or a group of formula (VII):

—NH—CO—Y (VII)

wherein Y represents a linear, saturated or unsaturated alkyl chain in $C_{12}$ to $C_{18}$;
$R^2$ represents a hydrogen atom or a linear, branched and/or cyclic, saturated or unsaturated hydrocarbon group, including 1 to 20 carbon atoms, comprising one or more heteroatoms chosen from nitrogen, oxygen, sulfur, fluorine, chlorine, bromine or iodine; and having at least one functional cationic group;
$R^3$ represents a hydrogen atom or is identical to $R^1$, or is identical to $R^2$.

Among the amphiphilic derivatives of triazamacrocyclic compounds according to the invention, the following are especially preferred:
1,4-didodecyl-7-betainyl-1,4,7-triazacyclononane;
1,4-ditetradecyl-7-betainyl-1,4,7-triazacyclononane;
1,4-dihexadecyl-7-betainyl-1,4,7-triazacyclononane;
1,4-dioctadecyl-7-betainyl-1,4,7-triazacyclononane;
1,4-dioleyl-7-betainyl-1,4,7-triazacyclononane;
1,4-didodecyl-N(7'-carboxymethyl-1',4',7'-triazacyclononane)-L-aspartate;
1,5-didodecyl-N(7'-carboxymethyl-1',4',7'-triazacyclononane)-L-glutamate;
1,4-ditetradecyl-N(7'-carboxymethyl-1',4',7'-tri-azacyclononane)-L-aspartate;
1,5-ditetradecyl-N(7'-carboxymethyl-1',4',7'-tri-azacyclononane)-L-glutamate;
1,4-dihexadecyl-N(7'-carboxymethyl-1',4',7'-tri-azacyclononane)-L-aspartate;
1,5-dihexadecyl-N(7'-carboxymethyl-1',4',7'-tri-azacyclononane)-L-glutamate;
1,4-dioctadecyl-N(7'-carboxymethyl-1',4',7'-tri-azacyclononane)-L-aspartate;

1,5-dioctadecyl-N(7'-carboxymethyl-1',4',7'-tri-azacyclononane)-L-glutamate;
1,4-dioleyl-N(7'-carboxymethyl-1',4',7'-triaza-cyclononane)-L-aspartate;
1,5-dioleyl-N(7'-carboxymethyl-1',4',7'-triaza-cyclononane)-L-glutamate;
1,4-dioleyl-N(1',4'-dibetainyl-7'-carboxymethyl-1',4',7'-triaza-cyclononane)-L-aspartate;
1,5-dioleyl-N(1',4'-dibetainyl-7'-carboxymethyl-1',4',7'-triaza-cyclononane)-L-glutamate;
1,4-dioctadecyl-7-ornithyl-1,4,7-triazacyclononane;
1,4-dioleyl-7-ornithyl-1,4,7-triazacyclononane;
1,4-dioctadecyl-7-arginyl-1,4,7-triazacyclononane;
1,4-dioleyl-7-arginyl-1,4,7-triazacyclononane;
1,4-dioctadecyl-7-lysyl-1,4,7-triazacyclononane;
1,4-dioleyl-7-lysyl-1,4,7-triazacyclononane;
1,4-dioleyl-N(1',4'-ornithyl-1',4',7'-triaza-cyclononane-7'-carboxymethyl)-L-aspartate;
1,5-dioleyl-N(1',4'-ornithyl-1',4',7'-triaza-cyclononane-7'-carboxymethyl)-L-glutamate;
1,4-dioleyl-N(1',4'-arginyl-1',4',7'-triaza-cyclononane-7'-carboxymethyl)-L-aspartate; and
1,5-dioleyl-N(1',4'-arginyl-1',4',7'-triaza-cyclononane-7'-carboxymethyl)-L-glutamate;
1,4-dioleyl-N(1',4'-diornithyl-7'-carboxymethyl-1',4',7'-triazacyclononane)-L-aspartate;
1,5-dioleyl-N(1',4'-diornithyl-7'-carboxymethyl-1',4',7'-triazacyclononane)-L-glutamate;
1,4-dioleyl-N(1',4'-diarginyl-7'-carboxymethyl-1',4',7'-triazacyclononane)-L-aspartate;
1,5-dioleyl-N(1',4'-diarginyl-7'-carboxymethyl-1',4',7'-triazacyclononane)-L-glutamate;
1-octadecyl-4-oleyl-7-betainyl-1,4,7-triazacyclononane;
1-octadecyl-5-oleyl-N(7'-carboxymethyl-1',4',7'-triaza-cyclononane)-L-glutamate;
1-octadecyl, 4-oleyl-N(7'-carboxymethyl-1',4',7'-triaza-cyclononane)-L-aspartate;
1-dodecyl-4-oleyl-7-betainyl-1,4,7-triazacyclononane;
1-oleyl-4-dodecyl-7-betainyl-1,4,7-triazacyclononane.

Advantageously, the derivatives according to the invention may include groups enabling their solubility, their cell penetration and their bioavailability to be enhanced.

The invention also relates to the use of a derivative as described above, as a carrier of active molecules.

The active molecules capable of being used include any drug, i.e. any substance capable of being used in humans or animals and capable of being administered to them, in order to establish a medical diagnosis or restore, correct or modify their physiological functions by exerting a pharmacological, immunological or metabolic action.

As non-limiting examples of active molecules capable of being used, it is possible to cite, in particular, proteins such as antibodies, nucleic acids such as genes or siRNA, but also antitumor agents such as bortezomib, cisplatin, carboplatin, ifosfamide, chlorambucil, busulfan, thiotepa, 5-fluorouracil (5FU), fludarabine, methotrexate, vincristine, vinblastine, vinorelbine, paclitaxel, docetaxel, camptothecin derivatives, amsacrine, anthracyclines, epipodophyllotoxin derivatives, doxorubicin, daunorubicin, actinomycin-D, mitomycin-C, plicamycin and bleomycin. It is also possible to cite the ITK's used in different tumor pathologies such as, for example, Imatinib, Dasatinib, Nilotinib and Sunitinib.

Advantageously, the derivatives of the invention are capable of being used as a carrier of nucleic acids or therapeutic molecules such as proteins. More preferably, the derivatives of the invention are used as antibody carriers.

The invention also relates to a pharmaceutical composition including an amphiphilic derivative as described above.
Preferably, said composition includes:
a derivative as described above;
a colipid; and
a pharmaceutically acceptable carrier.

As a non-limiting example of a colipid, it is possible to cite, advantageously, dioleoylphosphatidylethanolamine (DOPE).

The concentration of the colipid in the composition is advantageously between 0 and 50% by weight of the total weight of the composition. More preferably, the concentration of the colipid is between 0 and 30% by weight of the total weight of the composition. Still more preferably, the concentration of the colipid is between 5 and 10% by weight of the total weight of the composition.

The composition is advantageously in the form of an aqueous dispersion of nanoparticles.

The invention also relates to a product including, on the one hand, at least one derivative as described above and, on the other hand, at least one active molecule as described above, as a drug. This type of product may also be called a nanodrug. As indicated above, a nanodrug may be defined as a carrier or a vector of nanometric size capable of carrying an active molecule to a given therapeutic target: a gene, a protein, a cell, a tissue or an organ.

Thus, the invention also relates to a nanodrug including, on the one hand, at least one derivative as described above and, on the other hand, at least one active molecule as described above.

The invention also relates to such a nanodrug for the treatment of autoimmune diseases or for the treatment of cancer.

The invention also relates to a product containing, on the one hand, a nanodrug and, on the other hand, at least one pharmaceutical compound, as a combination product for simultaneously, separate or sequential administration, for the transport of molecules of therapeutic interest, in particular the intracellular delivery of antibodies.

Advantageously, the pharmaceutical compound according to the invention is an anti-inflammatory agent, or an agent reducing the secondary effects associated with the nanodrugs or the active molecules according to the invention.

By simultaneous therapeutic use, in this invention, we mean an administration of both the nanodrug and at least one pharmaceutical compound, by the same route and at the same time or substantially the same time.

By separate therapeutic use, in this invention, we mean in particular an administration of the nanodrug according to the invention and a pharmaceutical compound, at the same time or substantially the same time by different routes.

By sequential therapeutic use, we mean an administration of the nanodrug according to the invention and a pharmaceutical compound at different times, the route of administration being identical or different. More specifically, we mean a mode of administration according to which the entire administration of the nanodrug according to the invention or of a pharmaceutical compound is completed before the administration of the other begins.

It is thus possible to administer the nanodrug according to the invention or a pharmaceutical compound over several months before administering the other. There is no simultaneous treatment in this case. It is also possible to envisage an alternate administration of the nanodrug according to the invention or of the pharmaceutical compound over several weeks.

The route of administration of the composition according to the invention can be oral, parenteral, topical or ocular. Preferably, the pharmaceutical composition is prepared in a form suitable for parenteral application.

Thus, by parenteral route, the composition may be in the form of solutions or suspensions for perfusion or for intramuscular, intravenous or subcutaneous injection.

Alternatively, the composition may be administered orally and may be in the form of tablets, capsules, sugar-coated tablets, syrups, suspensions, solutions, powders, granules, emulsions, suspensions of microspheres or nanospheres or lipid or polymer vesicles allowing controlled release.

Also alternatively, when the composition according to the invention is administered topically, the pharmaceutical composition according to the invention is more specifically intended for the treatment of skin and mucous membranes and may be in liquid, pasty or solid form and more specifically in the form of ointments, aqueous, alcoholic or oily solutions, dispersions of the lotion type, aqueous, anhydrous or lipophilic gels, powders, impregnated pads, detergents, wipes, sprays, foams, sticks, shampoos, compresses, cleansing bases, emulsions of liquid or semi-liquid consistency of the milk type, obtained by dispersion of a fatty phase in an aqueous phase (O/W) or the reverse (W/O), or suspensions or emulsions of soft, semi-liquid or solid consistency of the cream, gel or pomade type. It may also be in the form of suspension of microspheres or nanospheres or lipid or polymer vesicles or polymer or gel patches allowing controlled release.

Finally, the invention also relates to methods for synthesis of the amphiphilic derivatives according to the invention. Such synthesis methods are described in the examples below.

EXAMPLE 1: SYNTHESIS OF COMPOUNDS ACCORDING TO THE Invention

1. Material:

Most of the reagents and solvents come from Alfa Aesar GmbH (Bischheim, France), Merck KgaA (Darmstadt, Germany), VWR Prolabo (Briare, France), Sigma-Aldrich (Saint Quentin Fallavier, France) and Fluka (division of Sigma-Aldrich, Saint Quentin Fallavier, France). Triazacyclononane (TACN) comes from CheMatech (Dijon, France). All of the anhydrous solvents are purchased at Merck and used as is.

2. Methods a) Chromatography

Thin Layer Chromatography (TLC) is performed on aluminum plates 5×7.5 cm coated with silica gel 60 F254 (Merck). The compounds are revealed under UV light ($\lambda$=254 nm), then by spraying an aqueous solution of 10% sulfuric acid followed by a step of heating at 250° C. for all of the lipid derivatives, or by aspersion of a 0.2% solution of ninhydrin in ethanol followed by a step of heating at 250° C. for compounds having an amine function.

The flash chromatographic separations are performed on silica gel 60 (230-400 Mesh ASTM) (Merck).

b) Mass Spectrometry

Preparation of the Samples

The products to be analyzed are dissolved (0.01 mg/mL) in a mixture of methanol/water 1/1 (v/v) or acetonitrile/water 1:1 (v/v) and the solutions are directly introduced into the electrospray source (at 5 μL/min) by means of a syringe pump (Harvard Apparatus, Les Ulis, France).

Equipment

The exact mass measurements are performed on a Waters-Micromass device (Manchester, U.K.) LCT, equipped with a pneumatically assisted electrospray (Z-spray) ion source, and provided with an additional nebulizer (Lockspray) for the reference compound (NaI). Nitrogen is used as the desolvation and nebulization gas with a flow rate of 500 and 20 L/h, respectively. The temperatures of the source and the desolvation gas are respectively set at 80 and 120° C. The capillary voltage is ±3.0 kV and the cone voltage is ±100 V (±ESI). The spectra are accumulated at a rate of 3 seconds per scan for a mass range of between 100 and 3500 uma. The resolution used is 5000 FWHM.

The acquisition of data and processing thereof are performed with the MassLynx V3.5 program.

c) NMR $^1$H

The proton NMR experiments are recorded at a frequency of 400.13 Mhz on a BRUKER Avance DRX400 device equipped with an inverse broadband probe (BBI). The chemical movements are given with respect to an external reference, tetramethylsilane ($\delta$=0 ppm), and the internal calibrations are performed using the residual solvent signal. The solvents deuterated solvents used (CDC13, DMSO-d6) come from Eurisotop (Gif sur Yvette, France). The measurements are performed using a rigorous temperature control at 298 K (±0.1 K).

The spectra are acquired on 16 K points, and converted to 32 K points (zero-filling). An optional treatment with an exponential function (1<LB<5) or a Gaussian function (0.1<GB<0.3; −3<LB<−1) is performed on each of the spectra, as well as a correction of the baseline.

The spectra are processed on a PC using the MestReNova software (Mestrelab Research S.L., Santiago de Compostela, Spain).

3. Examples of Synthesis Methods a) Synthesis of 1,4-didodecyl-7-betainyl-1,4,7-triazacyclononane (1) (DL-TACN-Bet)

The synthesis method shown in FIG. 1 makes it possible to obtain the title compound, or compound 1, of formula:

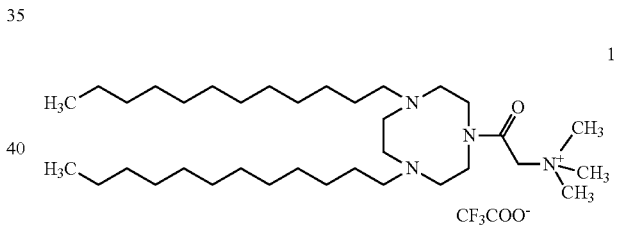

from commercial 1,4,7-triazacyclononane i) Step 1: Preparation of 1,4-di(tert-butoxycarbonyl)-1,4,7-triazacyclononane (1a)

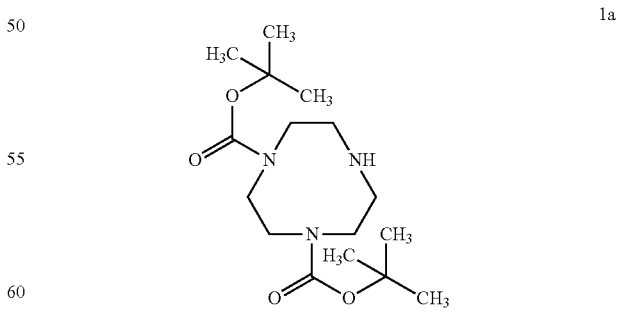

Triethylamine (460 pL; 3.30 mmol) is added to a solution of 1,4,7-triazacyclononane (TACN) (320.8 mg; 2.48 mmol) in chloroform (20 mL) under agitation and under an inert atmosphere. A solution of di-tert-butyl dicarbonate (1 g; 4.58 mmol) in chloroform (10 mL) is then added very slowly, over a period of 4 h, to the reaction medium. The mixture is then kept under agitation for one night at room temperature and under an inert atmosphere. The solvents are then dry evaporated under a primary vacuum, until a white solid residue is obtained, which is purified by silica gel chromatography (ethyl acetate/methanol 10/1 v/v). The pure compound 1a is thus isolated (521.2 mg; 70%), in the form of a colorless oil.

TLC: Rf=0.5 (CH$_2$Cl$_2$/MeOH 9/1 v/v).

HRMS (ESI$^+$): m/z measured at 330.2394 [M+H]$^+$; calculated at 330.2393 for C$_{16}$H$_{32}$N$_3$O$_4$.

NMR $^1$H (CDCl$_3$) δ (ppm): 1.41 (s, 18H, CH$_3$); 2.85-2.87 (m, 4H, CH$_2$); 3.15-3.22 (m, 4H, CH$_2$); 3.35-3.42 (m, 4H, CH$_2$).

ii) Step 2: Preparation of
3-betainylthiazolidine-2-Thione Chloride (1b)

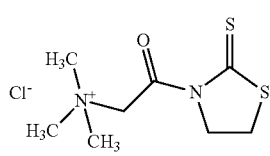

1b

A thionyl chloride solution (1.8 g; 15 mmol) in anhydrous acetonitrile (20 mL) is added drop by drop to the reaction medium containing the glycine betaine (1.17 g; 10 mmol) in suspension in the anhydrous acetonitrile (5 mL), the glycine betaine being first dried at 50° C. for 4 days. The mixture is then kept at 35-40° C. for 1 h under agitation and under an inert atmosphere. The reaction medium is then concentrated under a primary vacuum, then the resulting acyl chloride is dissolved in anhydrous dichloromethane (10 mL). 2-mercaptothiozoline (1.31 g; 11 mml) and triethylamine (1 g; 10 mmol), previously dissolved in 60 mL of anhydrous dichloromethane, are added at 0° C. to the previous solution. The reaction medium is then kept under agitation for 30 minutes at room temperature and under an inert atmosphere.

After concentration of the medium under a primary vacuum, the precipitate formed is washed twice with boiling dichloromethane, then filtered on a frit to yield activated glycine 1b (1.66 g; 65%), in the form of a yellow powder.

TLC: Rf=0.7 (MeOH).

HRMS (ESI$^+$): m/z measured at 219.0623 [M]$^+$; calculated at 219.0626 for C$_8$H$_{15}$N$_2$OS$_2$.

NMR $^1$H (DMSO-d6) δ (ppm): 3.30 (s, 9H, CH$_3$); 3.49 (t, 2H, CO—N—CH$_2$, J=7.6 Hz); 4.57 (t, 2H, CH$_2$—S, J=7.6 Hz); 5.27 (s, 2H, N$^+$—CH$_2$—CO).

iii) Step 3: Preparation of 1,4-di(tert butoxycarbonyl)-7-betainyl-1,4,7-triazacyclononane (1c)

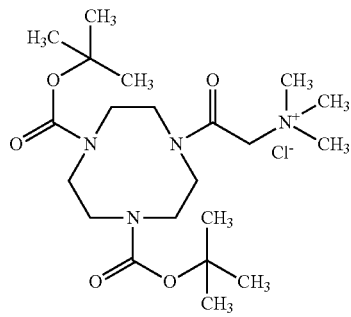

1c

Triethylamine (1 mL; 7.2 mmol) is added to a solution of 1,4-di(tert-butoxycarbonyl)-1,4,7-triazacyclononane 1a (150 mg; 0.46 mmol) in N,N-dimethylformamide (DMF) (10 mL) under agitation and under an inert atmosphere. 3-betainylthiazolidine-2-thione chloride 1b (175.8 mg; 0.69 mmol) is then added directly into the reaction medium. The mixture is then kept under agitation for one night at room temperature and under an inert atmosphere. The solvents are then dry evaporated under a primary vacuum. The residue obtained is finally purified by silica gel chromatography (ethyl acetate). The compound 1c is thus isolated in the form of a white solid (chloride salt) (117.3 mg; 55%).

TLC: Rf=0.5 (CH$_2$Cl$_2$/MeOH 9/1 v/v).

HRMS (ESI+): m/z measured at 429.3074 [M]+; calculated at 429.3077 for C$_{21}$H$_{41}$N$_4$O$_5$.

iv) Step 4: Preparation of
7-betainyl-1,4,7-triazacyclononane (1d)

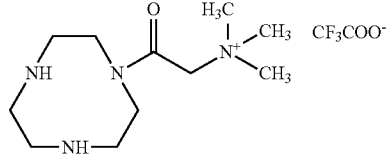

1d

Trifluoroacetic acid (1 mL) is added to a solution of 1,4-di(tert-butoxycarbonyl)-7-betainyl-1,4,7-triazacyclononane 1c (110 mg; 0.24 mmol) in dichloromethane (1 mL) under agitation. The reaction is kept under agitation for 30 minutes at room temperature. The reaction medium is then concentrated under a primary vacuum, redissolved in dichloromethane and again concentrated under a primary vacuum. The operation is repeated several times in order to remove any traces of trifluoroacetic acid. The residue is dried for one night under a primary vacuum. The pure compound 1d (135 mg; quantitative) is obtained in the form of a pale yellow oil.

TLC: Rf=0 (CH$_2$Cl$_2$/MeOH 9/1 v/v).

HRMS (ESI+): m/z measured at 230.2109 [M+H]+; calculated at 230.2107 for C$_{11}$H$_{26}$N$_4$O.

v) Step 5: Preparation of Didodecyl Triflate (1e)

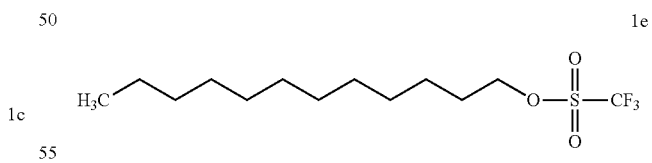

1e

Trifluoromethanesulfonic anhydride (1.8 g; 1.07 mL; 6.5 mmol) then anhydrous pyridine (0.51 g; 525 µL; 6.5 mmol) are successively added to an anhydrous dichloromethane solution (10 mL) cooled in an ice bath at 0° C., under agitation and under an inert atmosphere. During this addition, a release of smoke is observed and a white precipitate forms in the reaction medium. The ice bath is then removed, then a solution of lauric alcohol (0.93 g; 5 mmol) in anhydrous dichloromethane (4 mL) is added drop by drop into the reaction medium under agitation. The mixture is kept under agitation for 2 hours at room temperature, then the reaction is quenched by adding water. Dichloromethane (20 mL) is added to the reaction medium, and the solution is washed with water (2×10 mL). The aqueous phases are re-extracted with dichloromethane (2 mL) and the organic phases are regrouped, washed with brine (10 mL), dried on sodium sulfate, then filtered on filter paper. The filtrate is evaporated with the Rotavapor to obtain a brown oil. The oil is redissolved in hexane (2 mL) and loaded onto a silica column. The final product is eluted with a mixture of ether/hexane 1/1 v/v, taking care not to produce colored secondary products that are co-eluted with the product. The solvents are dry evaporated with the Rotavapor and the pure product 1e (1.41 g; 89%) is obtained in the form of a colorless oil.

TLC: Rf=0.7 (Hexane/Ether 1/1 v/v).

RMN $^1$H (CDCl$_3$) δ (ppm): 4.56 (t, 2H, CF$_3$SO$_3$CH$_2$); 1.91-1.79 (m, 2H, CF$_3$SO$_3$CH$_2$CH$_2$); 1.53-1.20 (m, 18H, CH2 (lauryl)); 0.91 (t, 3H, CH$_3$).

The instability of this product over time requires it to be used very quickly for the next synthesis step.

vi) Step 6: Preparation of
1,4-didodecyl-7-betainyl-1,4,7-triazacyclononane
(1)

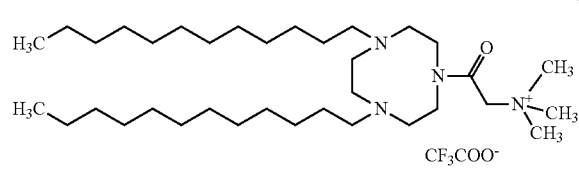

Diisopropylethylamine (78 μL; 0.45 mmol) is added to a solution of 7-betainyl-1,4,7-triazacyclononane 1d (50 mg; 0.09 mmol) in anhydrous chloroform (10 mL) under agitation and under an inert atmosphere. Didodecyltriflate 1e (143.3 mg; 0.45 mmol), freshly prepared from lauric alcohol and triflic anhydride, is added to the reaction medium. The mixture is then kept under agitation for one night at room temperature and under an inert atmosphere. The solvents are then dry evaporated under a primary vacuum. The residue obtained is finally purified by silica gel chromatography (dichloromethane/methanol 1/0 to 9/1 v/v). The pure compound 1 is thus isolated (41.4 mg; 86%) in the form of a white solid.

TLC: Rf=0.5 (CH$_2$Cl$_2$/MeOH 9/1 v/v).

HRMS (ESI$^+$): m/z measured at 566.5866 [M+H]$^+$; calculated at 566.5863 for C$_{35}$H$_{74}$N$_4$O.

b) Synthesis of 1,4-dioctadecenyl-7-betainyl-1,4,7-triazacyclononane (2) (DO-TACN-Bet)

Figure 2:
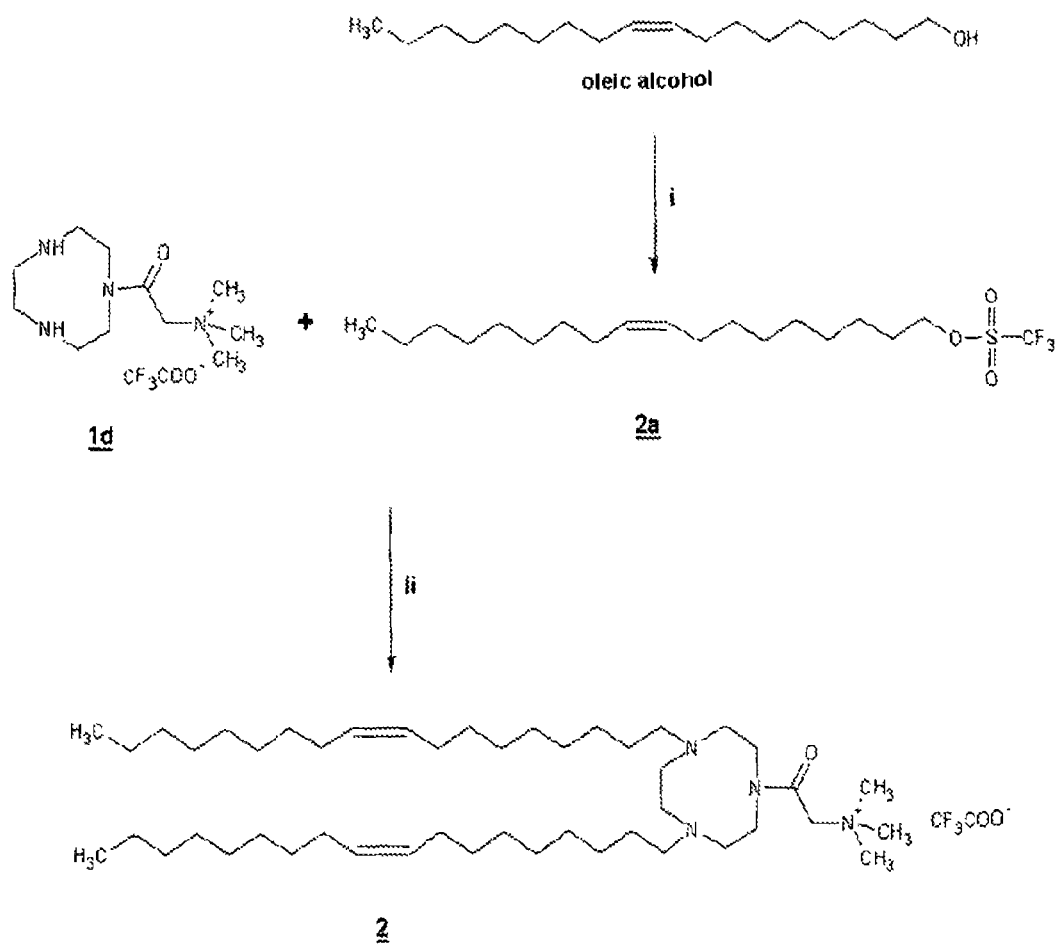
FIG. 2 shows the reaction scheme for the synthesis of 1,4-dioctadecenyl-7-betainyl-1,4,7-triazacyclononane.

The synthesis method shown in FIG. 2 makes it possible to obtain the title compound, or compound 2, of formula:

This compound 2 is obtained by coupling 7-betainyl-1,4,7-triazacyclononane (1d), the synthesis of which was previously described in point 3.a), with oleyl triflate (2a).

i) Step 1: Synthesis of Oleyl Triflate (2a)

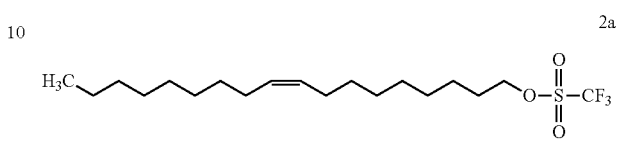

Trifluoromethanesulfonic anhydride (1.8 g; 1.07 mL; 6.5 mmol) then anhydrous pyridine (0.51 g; 525 μL; 6.5 mmol) are successively added to an anhydrous dichloromethane solution (10 mL) cooled in an ice bath at 0° C., under agitation and under an inert atmosphere.

During this addition, a release of smoke is observed and a white precipitate forms in the reaction medium. The ice bath is then removed, then a solution of oleic alcohol solution (1.34 g; 5 mmol) in anhydrous dichloromethane (4 mL) is added drop by drop to the reaction medium under agitation. The mixture is kept under agitation for 2 hours at room temperature, then the reaction is quenched by adding water. Dichloromethane (20 mL) is added to the reaction medium, and the solution is washed with water (2×10 mL). The aqueous phases are re-extracted with dichloromethane (2 mL) and the organic phases are regrouped, washed with brine (10 mL), dried on sodium sulfate, then filtered on filter paper. The filtrate is evaporated with the Rotavapor in order to obtain a clear brown liquid. The liquid residue is re-dissolved in hexane (2 mL) and loaded onto a silica column. The final product is eluted with a mixture of ether/hexane 1/1 v/v, taking care not to produce colored secondary products that are co-eluted with the product. The solvents are dry evaporated with the Rotavapor, and a pure product 2a (1.30 g; 65%) is obtained in the form of a colorless liquid.

TLC: Rf=0.8 (Hexane/Ether 1/1 v/v).

NMR $^1$H (CDCl$_3$) δ (ppm): 5.42-5.33 (m, 2H, CH=CH); 4.54 (t, 2H, CF3SO3CH$_2$); 2.13-1.93 (m, 4H, CH$_2$CH=CHCH$_2$); 1.90-1.69 (m, 2H, CF3SO3CH$_2$CH$_2$); 1.54-1.12 (m, 22H, CH$_2$ (oleyl)); 0.89 (t, 3H, CH$_3$).

The instability of this product over time requires it to be used very quickly for the next synthesis step.

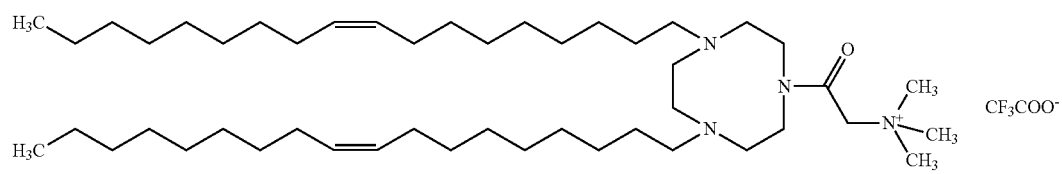

ii) Step 2: Synthesis of 1,4-dioctadecenyl-7-betainyl-1,4,7-triazacyclononane (2)

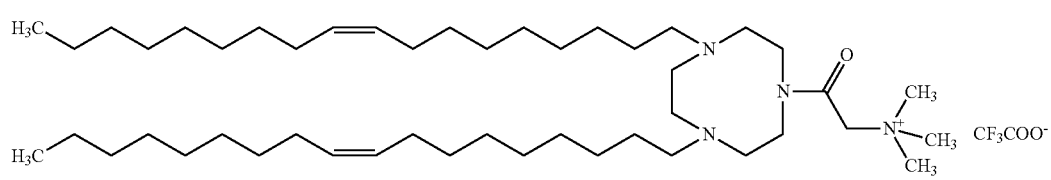

Diisopropylethylamine (78 µL; 0.45 mmol) is added to a solution of 7-betainyl-1,4,7-triazacyclononane 1d (50 mg; 0.09 mmol) in anhydrous chloroform (10 mL) under agitation and under an inert atmosphere. Oleyl triflate 2a (180.3 mg; 0.45 mmol), freshly prepared from oleic alcohol and triflic anhydride, is then added directly to the reaction medium. The mixture is then kept under agitation for one night at room temperature and under an inert atmosphere. The solvents are then dry evaporated under a primary vacuum. The residue obtained is finally purified by silica gel chromatography (dichloromethane/methanol 1/0 to 9/1 v/v). The pure compound 2 (53.0 mg; 94%) is thus isolated, in the form of an oil.

TLC: Rf=0.5 (CH$_2$Cl$_2$/MeOH 9/1 v/v)

HRMS (ESI$_+$): m/z measured at 730.7428 [M+H]$_+$; calculated at 730.7428 for C$_{47}$H$_{94}$N$_4$O.

c) Synthesis of 1,5-dioleyl-N(7'-carboxymethyl-1', 4',7'-triazacyclononane)-L-glutamate (3) (DOG-TACN)

Figure 3:
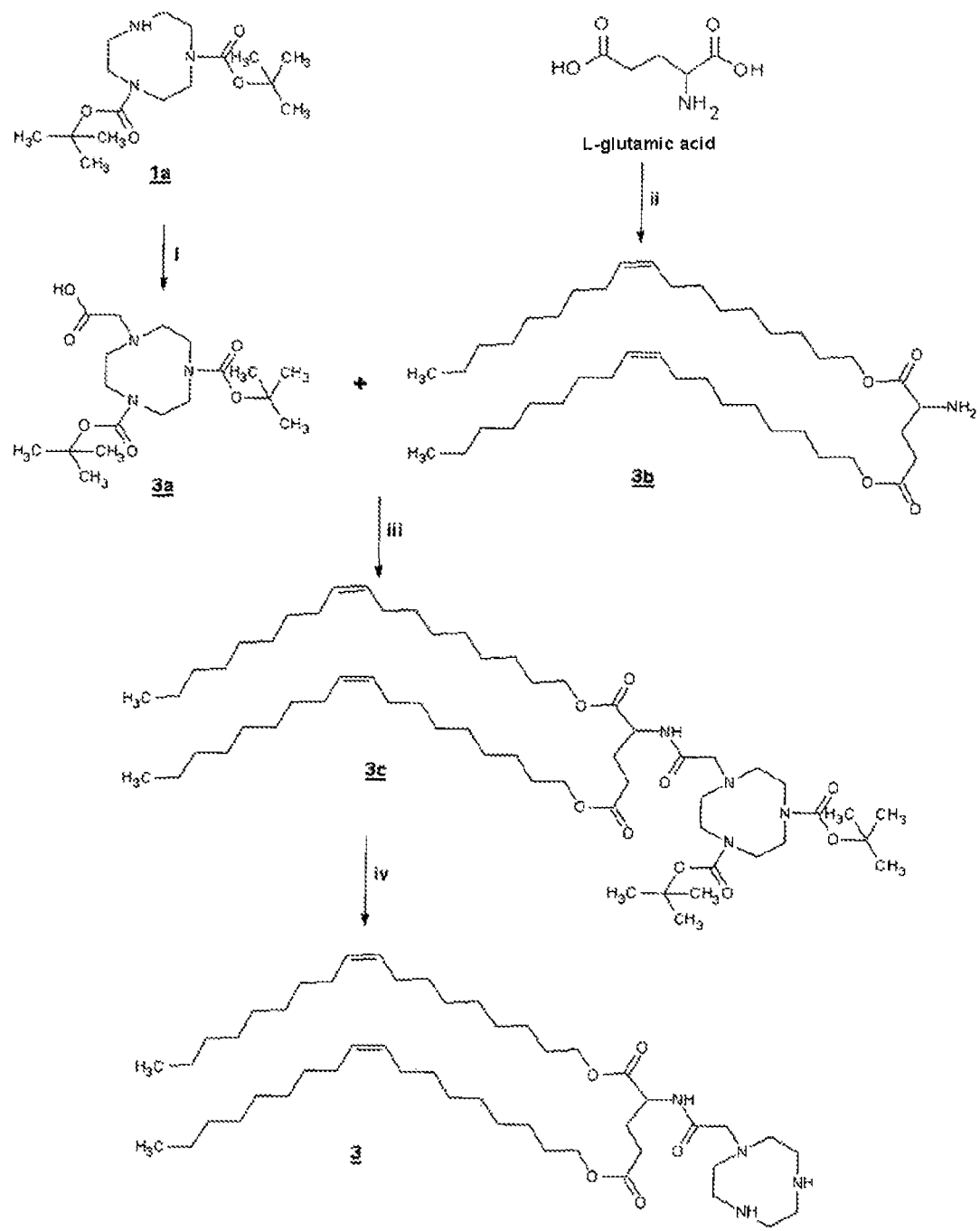
FIG. 3 shows the reaction scheme for the synthesis of 1,5-dioleyl-N(7'-carboxymethyl-1',4',7'-triazacyclononane)-L-glutamate.

The synthesis method shown in FIG. 3 makes it possible to obtain the title compound, or compound 3, of formula:

This compound 3 is obtained from 1,4-di(tert-butoxycarbonyl)-1,4,7-triazacyclononane (1a), the synthesis of which has previously been described in point 3.a).

i) Step 1: Preparation of 1,4-di(tert-butoxycarbonyl)-7-carboxymethyl-1,4,7-triazacyclononane (3a)

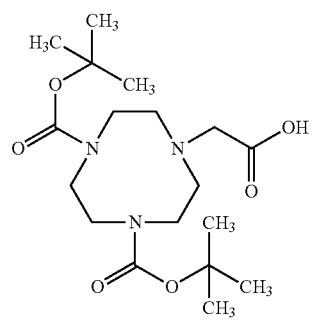

Sodium carbonate (67 mg; 0.63 mmol) and ethyl bromoacetate (70 µL; 0.63 mmol) are successively added to a solution of 1,4-di(tert-butoxycarbonyl)-1,4,7-triazacyclononane 1a (173.6 mg; 0.53 mmol) in acetonitrile (10 mL). The mixture is then brought to reflux (bath temperature=80° C.) and kept under agitation for one night at reflux. Then, the reaction is cooled to room temperature and the insoluble products are removed by filtration. The solution is concentrated under a primary vacuum, and the crude product is

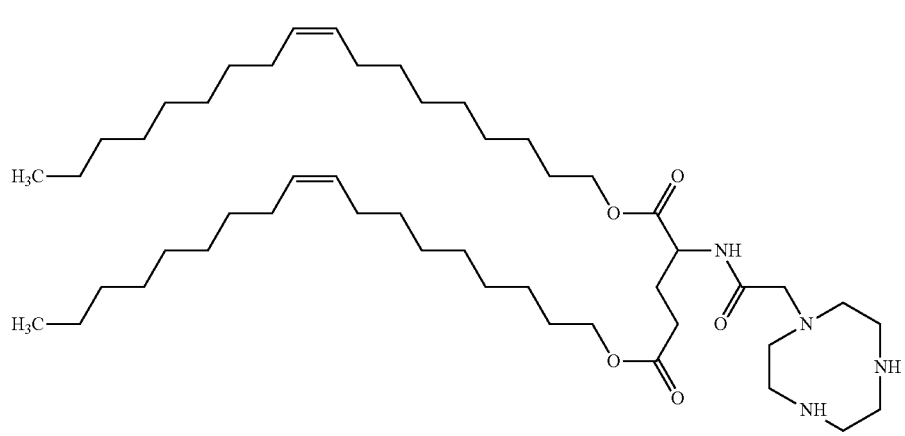

purified by silica gel chromatography (ethyl acetate) in order to produce the intermediate ester (194 mg; 88%) in the form of a pale yellow oil.

TLC: Rf=0.8 (CH$_2$Cl$_2$/MeOH 9/1 v/v).

HRMS (ESI$_+$): m/z measured at 416.2758 [M+H]$_+$; calculated at 416.2761 for C$_{20}$H$_{38}$N$_3$O$_6$.

Ester (194 mg; 0.47 mmol) is dissolved in methanol (5 mL), then a 1 mol/L (3 mL) soda solution is added to the solution under agitation. The mixture is kept under agitation for 2 h at room temperature. The methanol is then evaporated under vacuum, and the pH of the resulting aqueous solution is adjusted to 5 by adding a 5% citric acid solution (m/v). The aqueous phase is then extracted with dichloromethane (3×20 mL), the organic phases are combined, dried on anhydrous sodium sulfate, and the filtrate is concentrated under a primary vacuum in order to obtain the pure compound 3a (160 mg; 88%), in the form of a colorless oil.

TLC: Rf=0.4 (CH$_2$Cl$_2$/MeOH 9/1 v/v).

HRMS (ESI$_+$): m/z measured at 388.2452 [M+H]$_+$; calculated at 388.2448 for C$_{18}$H$_{34}$N$_3$O$_6$.

NMR $^1$H (CDCl$_3$) δ (ppm): 1.30-1.50 (m, 18H, C(CH$_3$)$_3$(Boc)); 3.10-3.60 (m, 14H, CH$_2$(TACN), NCH$_2$CO); 8.20 (br s, 1H, OH).

ii) Step 2: Preparation of 1,5-dioleyl-L-glutamate (3b)

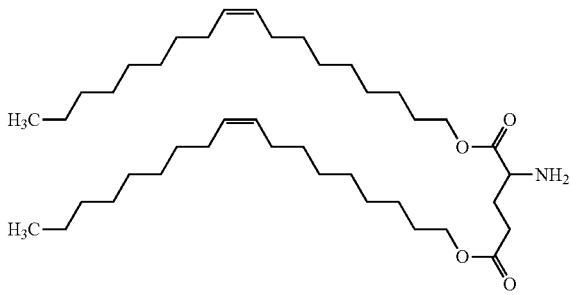

3b

L-glutamic acid (0.5 g; 3.4 mmol) and paratoluenesulfonic acid (0.780 g; 4.1 mmol) are dissolved in toluene (100 mL). The mixture is then brought to reflux (bath temperature=120° C.) under agitation for 1 h. The oleic alcohol (2.01 g; 7.5 mmol) is then introduced into the reaction medium, then the reaction is kept under agitation and at reflux for one night. The reaction is then cooled to room temperature, then the toluene is dry evaporated under a primary vacuum. The residue obtained is dissolved in chloroform (50 mL) and washed successively with a saturated aqueous solution of sodium bicarbonate (2×25 mL) with brine (1×25 mL). The organic phase is dried on anhydrous sodium sulfate, and the filtrate is concentrated under a primary vacuum in order to obtain a crude product that is purified by silica gel chromatography (dichloromethane/methanol 4/1 to 1/1 v/v). The pure compound 3b is thus isolated (0.45 g; 20%), in the form of a pale yellow oil.

TLC: Rf=0.4 (CH$_2$Cl$_2$/MeOH 98/2 v/v).

HRMS (ESI$_+$): m/z measured at 648.4931 [M+H]$_+$; calculated at 648.4931 for C$_{41}$H$_{78}$NO$_4$.

NMR $^1$H (CDCl$_3$) δ (Ppm): 0.90 (t, 6H, CH$_2$CH$_3$ (oleyl)); 1.26 (m, 44H, CH$_2$ (oleyl)); 1.57 (m, 4H, COOCH$_2$CH$_2$ (oleyl)); 1.90-2.12 (m, 2H, NH$_2$CHCH$_2$ (glutamate)); 2.04 (m, 8H, CH$_2$CH=CHCH$_2$ (oleyl)); 2.47 (t, 2H, CH$_2$CO (glutamate)); 3.59 (t, 1H, NH$_2$CH (glutamate)); 4.06-4.15 (t, 4H, COOCH$_2$ (oleyl)); 5.32-5.42 (m, 4H, CH=CH (oleyl)); 7.18, 7.73 (d, 2H, NH$_2$).

iii) Step 3: Preparation of 1,5-dioleyl-N(1',4'-di(tert-butoxycarbonyl)-7'-carboxymethyl-1',4',7'-triazacyclononane)-L-glutamate (3c)

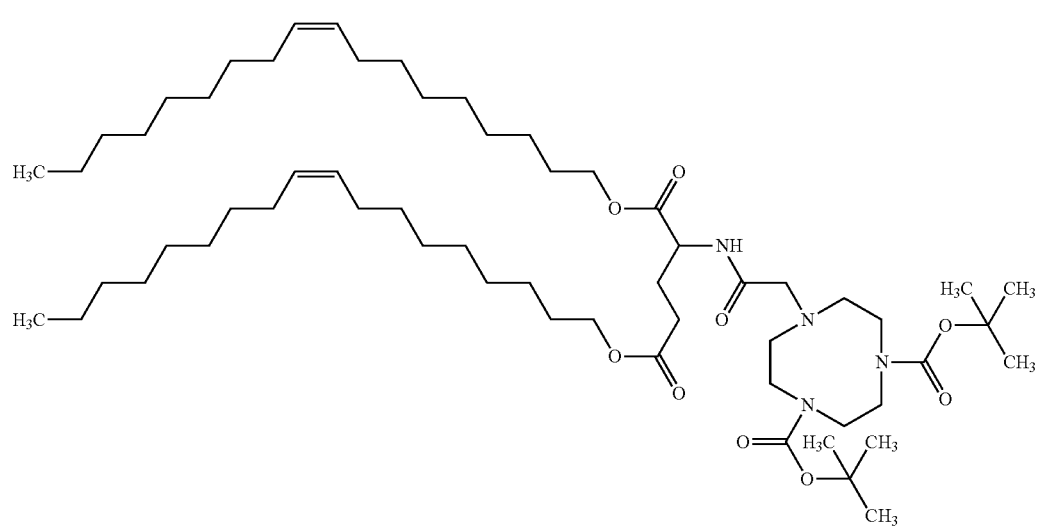

3c

PyBOP (72 mg; 0.138 mmol), 1,5-dioctadecenyl-L-glutamate 3b (97.3 mg; 0.150 mmol) and diisopropylethylamine (66 μL; 0.380 mmol) are successively added to a solution of 1,4-di(tert-butoxycarbonyl)-7-carboxymethyl-1,4,7-triazacyclononane 3a (53.3 mg; 0.138 mmol) in anhydrous dichloromethane (2 mL) under agitation and under an inert atmosphere. The reaction is then kept under agitation and under an inert atmosphere for one night at room temperature.

HRMS (ESI$_+$): m/z measured at 817.7145 [M+H]$_+$; calculated at 817.7146 for $C_{49}H_{93}N_4O_5$.

d) Synthesis of 1,5-dioleyl-(1',4'-dibetainyl-1',4',7'-triazacyclononane-7'-carboxymethyl)-L-glutamate (DOG-TACN-(Bet)$_2$)

Figure 4:
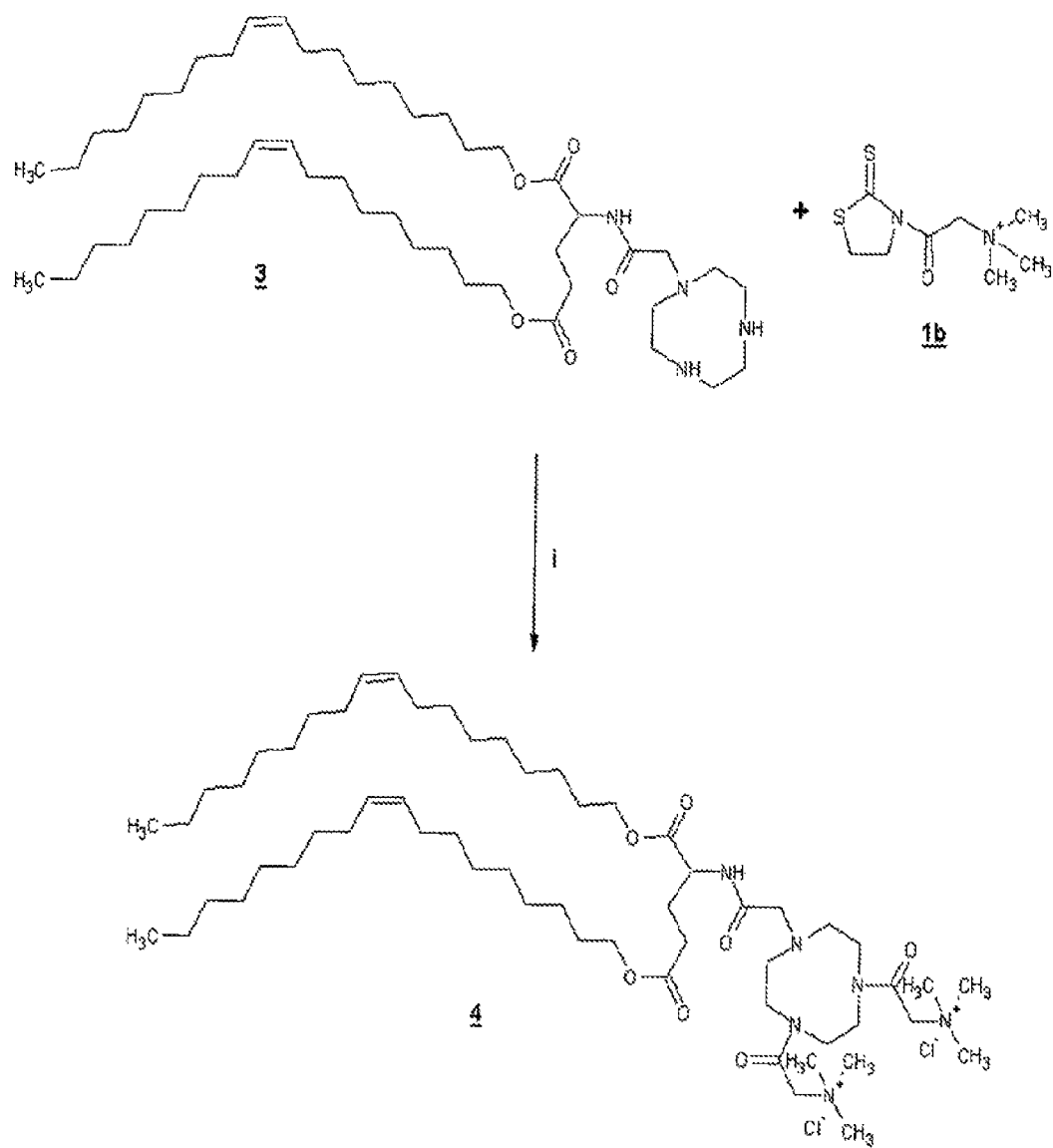
FIG. 4 shows the reaction scheme for the synthesis of 1,5-dioleyl-N(1',4'-dibetainyl-1',4',7'-triazacyclononane-7'-carboxymethyl)-L-glutamate.

The synthesis method shown in FIG. 4 makes it possible to obtain the title compound, or compound 4, of formula:

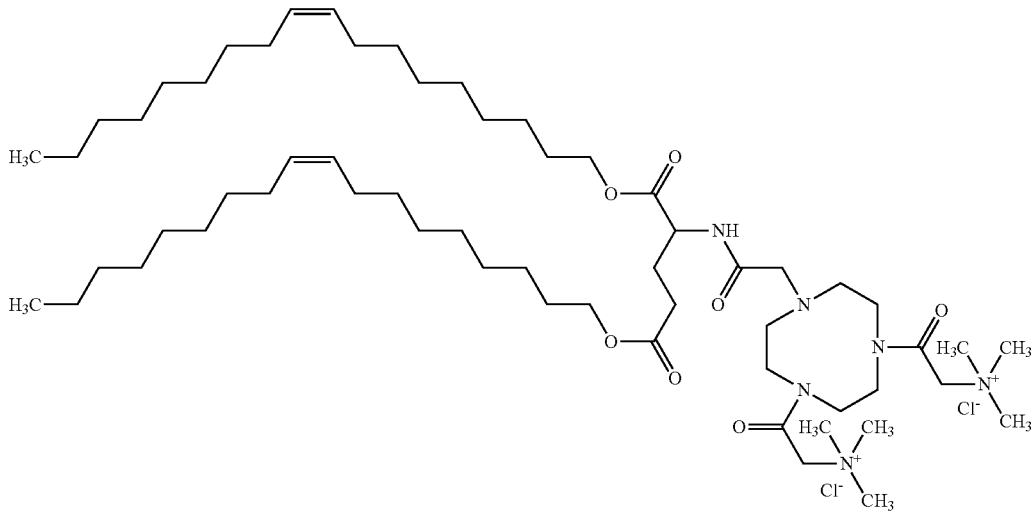 [SMILES: CCCCCCCC/C=C\CCCCCCCCOC(=O)CCC(NC(=O)CN1CCN(C(=O)C[N+](C)(C)C)CCN(C(=O)C[N+](C)(C)C)CC1)C(=O)OCCCCCCCC/C=C\CCCCCCCC ; [Cl-] ; [Cl-]]

The solvents are then dry evaporated under a primary vacuum, and the residue is purified by silica gel chromatography (dichloromethane/methanol 100/1 v/v). The pure compound 3c is thus isolated (124 mg; 88%), in the form of a yellow-orange oil.

TLC: Rf=0.8 (CH$_2$Cl$_2$/MeOH 95/5 v/v).

HRMS (ESI$_+$): m/z measured at 1019.8116 [M+H]$_+$; calculated at 1019.8113 for $C_{59}H_{109}N_3O_{10}$.

NMR $^1$H (CDCl$_3$) δ (ppm): 0.90 (t, 6H, CH$_2$CH$_3$ (oleyl)); 1.20-1.60 (m, 66H, C(CH$_3$)$_3$(Boc), CH$_2$ (oleyl), COOCH$_2$CH$_2$ (oleyl)); 1.90-2.12 (m, 2H, NH$_2$CHCH$_2$ (glutamate)); 2.04 (m, 8H, CH$_2$CH=CHCH$_2$ (oleyl)); 2.47 (t, 2H, CH$_2$CO (glutamate)); 3.10-3.60 (m, 15H, CH$_2$(TACN), NCH$_2$CO, NH$_2$CH (glutamate)); 4.06-4.15 (t, 4H, COOCH$_2$ (oleyl)); 5.32-5.42 (m, 4H, CH=CH (oleyl)); 7.29 (d, 1H, NHCO).

iv) Step 4: Preparation of 1,5-dioleyl-N(7'-carboxymethyl-1',4',7'-triazacyclononane)-L-glutamate (3) (DOG-TACN)

Trifluoroacetic acid (1 mL) is added to a solution of 1,5-dioctadecenyl-N(1',4'-di(tert-butoxycarbonyl)-7'-carboxymethyl-1',4',7'-triazacyclononane)-L-glutamate 3c (124 mg; 0.122 mmol) in dichloromethane (1 mL) under agitation. The reaction is kept under agitation for 30 minutes at room temperature. The reaction medium is then concentrated under a primary vacuum, re-dissolved in dichloromethane and again concentrated under a primary vacuum. The operation is repeated several times to remove all traces of trifluoroacetic acid. The residue is dried overnight under a primary vacuum. The pure compound 3 is obtained (126 mg; quantitative) in the form of a pale yellow oil.

TLC: Rf=0 (CH$_2$Cl$_2$/MeOH 95/5 v/v).

This compound 4 is obtained by coupling 3-betainylthiazolidine-2-thione chloride (1b) with 1,5-dioleyl-N(7'-carboxymethyl-1',4',7'-triazacyclononane)-L-glutamate (3), the syntheses of which have previously been described, respectively in points 3.a) and 3.c).

Triethylamine (1 mL; 7.2 mmol) is added to a solution of 1,5-dioctadecenyl-N(7'-carboxymethyl-1',4',7'-triazacyclononane)-L-glutamate 3 (100 mg; 0.097 mmol) in N,N dimethylformamide (DMF) (10 mL) under agitation and under an inert atmosphere. 3-betainylthiazolidine-2-thione chloride 1b (74.1 mg; 0.291 mmol) is then added directly to the reaction medium. The mixture is then kept under agitation for one night at room temperature and under an inert atmosphere. The solvents are then dry evaporated under a primary vacuum. The residue obtained is finally purified by silica gel chromatography (dichloromethane/methanol 95/5 to 8/2 v/v). The compound is thus isolated in the form of a white solid (24.2 mg; 23%).

TLC: Rf=0.4 (CH$_2$Cl$_2$/MeOH 9/1 v/v)

HRMS (ESI$_+$): m/z measured at 1017.8672 [M+H]$_+$; calculated at 1017.8671 for $C_{59}H_{113}N_6O_7$.

The example presented above describes the synthesis of triazacyclononane compounds containing a glycine betaine derivative. Similarly, compounds containing derivatives of arginine, lysine and ornithine have been produced. The efficacies of these compounds for the intracellular transport of antibodies differ according to the cell type used, but they are all more or less active. The presence of triacyclononane is essential for obtaining an effective compound.

EXAMPLE 2: BIOLOGICAL APPLICATIONS

1. Materials and Methods:

The dioleoylphosphatidylethanolamine (DOPE) comes from Sigma-Aldrich (Saint Quentin Fallavier, France). The antibodies to be delivered into the cells are Immunoglobulin G (IgG) from goat serum from Sigma-Aldrich and a p50 human anti-NFkB mouse IgG from BioLegend (San-Diego, Calif., USA). All of the culture media come from Lonza (Basel, Switzerland).

The efficacy of the transport of labeled antibodies into the cells is observed under fluorescence microscope.

2. Examples of Biological Applications Associated with the Transport of Antibodies into Living Cells a) Formulations of Amphiphilic Derivatives of Triazamacrocyclic Compounds According to the Invention in the Form of Nanoparticles in Water.

In a pill machine, one of the amphiphilic derivatives of triazamacrocyclic compounds described according to the invention is solubilized in chloroform in the presence of a colipid, dioleoylphosphatidylethanolamine (DOPE), in different molar ratios. The solvent is then evaporated under a light nitrogen current and the lipid film obtained is dried under a primary vacuum for at least 30 minutes. The lipid film is then rehydrated in sterile deionized water for 2 hours at room temperature. The suspension is finally sonicated by means of a sonicator equipped with a microprobe (Sonic Ruptor 250, OMNI International, Kennesaw, USA) in order to obtain an aqueous dispersion of nanoparticles.

The formulations are prepared at a concentration of 1 mmol/L of amphiphilic derivatives of triazamacrocyclic compounds in water. In the following examples, we will refer to formulations prepared "according to example 2.2a".

b) Influence of DOPE on the Efficacy of the Formulation

Multiple formulations are prepared according to example 2.2a with different molar ratios of DOPE, i.e. respectively with 0%, 5%, 10%, 20% and 50% DOPE. Cos-7 cells are seeded in a 24-well plate (100,000 cells/well) and cultivated in 500 μL of DMEM in the presence of serum in a CO2 incubator for 24 hours. The transport of antibodies is then performed as follows:

1 μg of immunoglobulin G (IgG) from fluorescein-labeled goat serum is diluted in 10 μL of PBS buffer.

2 μL of formulation prepared according to example 2.2a are added and the mixture is incubated for 15 minutes at room temperature.

90 μL of serum-free DMEM are then added and the final mixture is transferred onto the Cos-7 cells in culture.

The cells are then incubated in a CO2 incubator. The efficacy of the transport is viewed at 24 h and 48 h under fluorescence microscopy after the cells have been fixed with a formalin solution.

Figure 5:
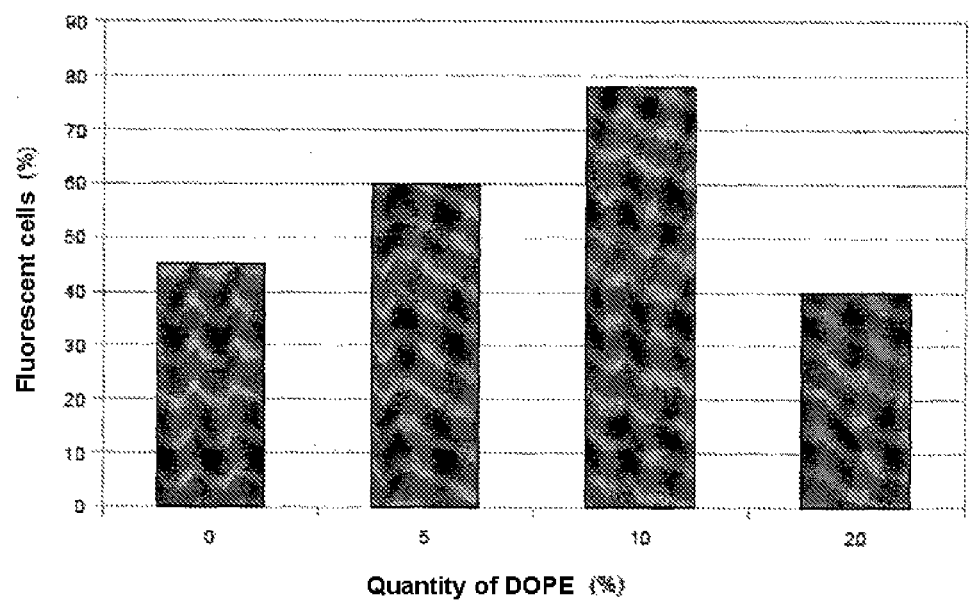
FIG. 5 shows the influence of the quantity of DOPE on the efficacy of the formulation of the compound.

For each formulation tested, the efficacy of the transport is measured at 5 h by flow cytofluorometry. The results presented in FIG. 5 show that the maximum efficacy is achieved with the formulation containing 10% DOPE.

c) Transport of a Fluorescent Antibody into Fibroblasts

NIH3T3 cells are seeded in a 24-well plate (100,000 cells/well) and cultivated in 500 μL of DMEM in the presence of serum in a CO2 incubator for 24 hours.

The transport of antibodies is then performed as follows:

1 μg of IgG from fluorescein-labeled goat serum is diluted in 10 μL of PBS buffer.

2 μL of formulation prepared according to example 2.2a are added and the mixture is incubated for 15 minutes at room temperature.

90 μL of serum-free DMEM are then added and the final mixture is transferred onto the NIH3T3 cells in culture.

The cells are then incubated in a CO2 incubator. The efficacy of the transport is viewed at 24 h and 48 h under fluorescence microscopy after the cells have been fixed with a formalin solution.

Figure 6A:
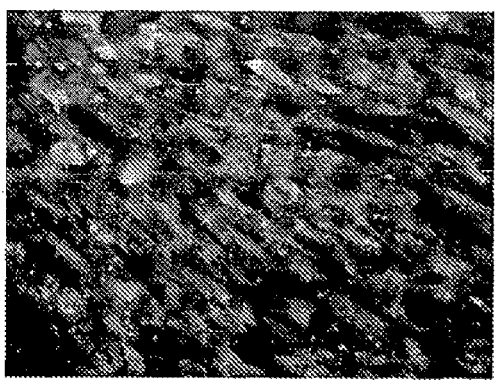
FIGS. 6a and 6b show the transport of fluorescent antibodies into NIH3T3 cells at 24 h (6a) and 48 h (6b)
Figure 6B:
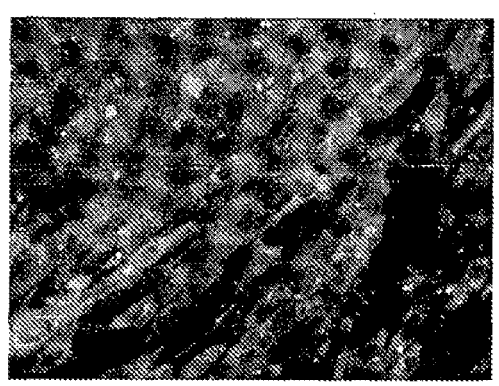

The results presented in FIGS. 6a and 6b show the fibroblasts of which the entire cytoplasm has been invaded by fluorescent antibodies. The labeling is intense, homogeneous and identical at 24 h and 48 h, the cells having continued their cell growth normally. The nucleus of the fibroblasts does not appear to contain antibodies.

d) Transport of Fluorescent Antibodies into Other Types of Cells

A549 and RAW264 cells are cultivated on a 24-well plate (100,000 cells/well). Different fluorescent antibodies are then delivered according to the protocol described in example 2.2b. The cells are observed under a fluorescent microscope after 5 h of incubation.

Figure 7A:
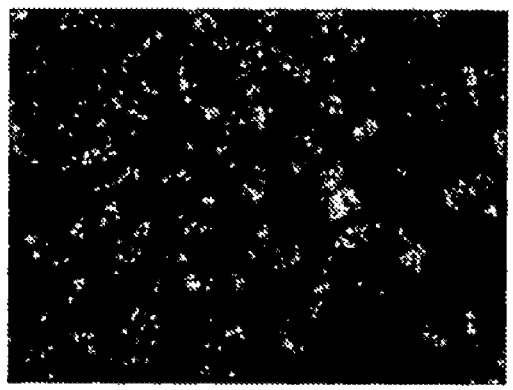
FIGS. 7a and 7b show the transport of fluorescent antibodies into A549 (7a) and RAW264 (7b) cells at 5 h.
Figure 7B:
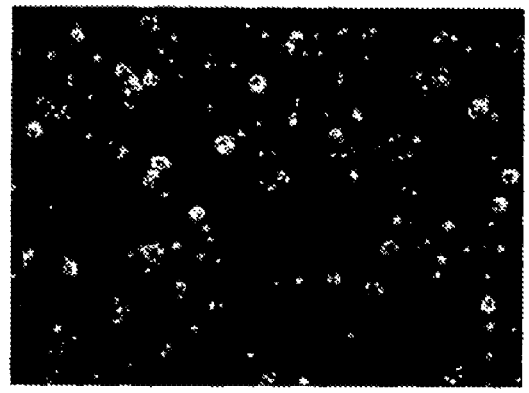

The results presented in FIGS. 7a and 7b show that the cells have clearly internalized the different antibodies.

e) Evaluation of the Cell Toxicity of the Compound

HeLa cells are seeded in a 96-well plate (10,000 cells/well) and cultivated in 100 μL of DMEM in the presence of serum in a CO2 incubator for 24 hours. The transport of antibodies is then performed as follows:

0.3 μg of IgG from fluorescein-labeled goat serum is diluted in 2.5 μL of PBS buffer.

0.3 μL of formulation prepared according to example 2.2a is added and the mixture is incubated for 15 minutes at room temperature.

20 μL of serum-free DMEM are then added and the final mixture is transferred onto the HeLa cells in culture.

The cells are then incubated in a CO2 incubator. The cell toxicity of the compound is measured at between 5 h and 48 h by an MTT test (3-(4,5-dimethylthiazol-2-yl)-2,5-diphenyl tetrasodium bromide). The 96-well plate is analyzed on a spectrophotometer at 540 nm.

Figure 8:
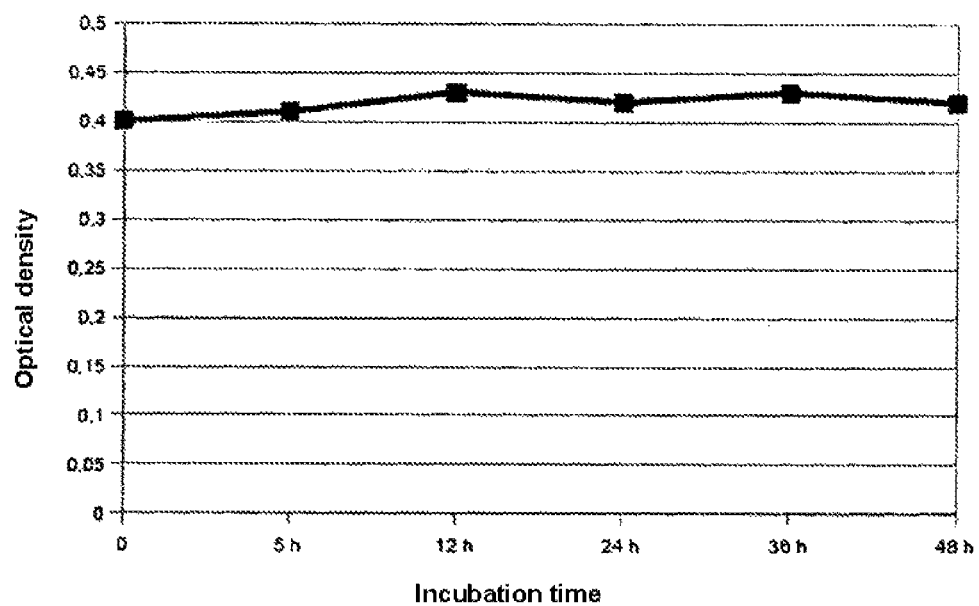
FIG. 8 shows the evaluation of the cellular toxicity of the compound on HeLa cells for 48 h.

The results presented in FIG. 8 show that the compound is not cytotoxic under these conditions of use.

f) Kinetics of the Transport of an Antibody

NIH3T3 cells are seeded in a 96-well plate (10,000 cells/well) and cultivated in 100 μL of DMEM in the presence of serum in a CO2 incubator for 24 hours. 0.3 μg of IgG from fluorescein-labeled goat serum is transported according to the protocol described in example 2.2e. The cells are then successively washed with PBS and with a trypsin solution, then centrifuged in order to remove as many free antibodies as possible, and are finally fixed with formalin. The intensity of the fluorescence is measured every 2 h, 3 h, 4 h then every 5 hours by a fluorometer at 525 nm.

Figure 9:
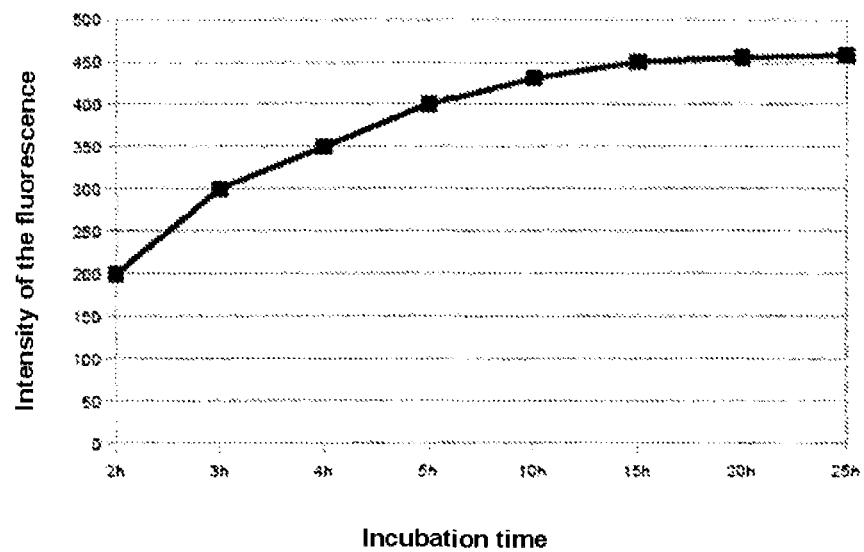
FIG. 9 shows the kinetics of the transport of antibodies on NIH3T3 cells.

The results presented in FIG. 9 show that the maximum quantity of antibodies present in the cells is reached in only several hours.

g) Influence of PBS on the Kinetics of Transport of an Antibody

VERO cells are seed in a 24-well plate (100,000 cells/well) and cultivated in 500 μL of DMEM in the presence of serum in a CO2 incubator for 24 hours.

The transport of antibodies is then performed as follows:

1 μg of IgG from fluorescein-labeled goat serum is diluted in 10 μL of PBS buffer.

1 μL of formulation prepared according to example 2.2a is added and the mixture is incubated for 15 minutes at room temperature.

190 μL of PBS are then added and the final mixture is transferred onto the NIH3T3 cells in culture.

The cells are then incubated at room temperature for 20 minutes, then the mixture is replaced with the DMEM culture medium with serum. The efficacy of the transport is viewed at 20 minutes under fluorescence microscopy.

Figure 10:
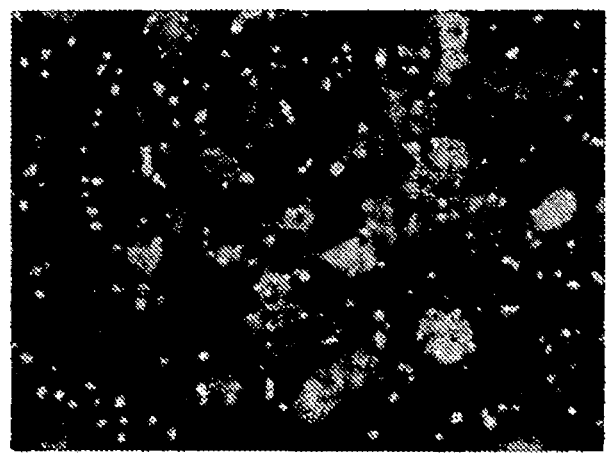
FIG. 10 shows the influence of PBS on the speed of transport of antibodies into VERO cells.

The results presented in FIG. 10 show that the antibody is delivered into the cells in culture much more quickly owing to the action of the PBS.

h) Influence of the Ionic Force of the Medium on the Efficacy of the Compound

A549 and BEAS-2B cells are seeded in a 24-well plate (100,000 cells/well) and cultivated in 500 µL of DMEM in the presence of serum in a CO2 incubator for 24 hours.

The transport of antibodies is then performed as follows:
1 µg of IgG from fluorescein-labeled goat serum is diluted in 10 µL of PBS buffer or 10 µL of PBS 0.5× buffer or in 10 µL of PBS 0.1× buffer.
2 µL of formulation prepared according to example 2.2a are added and the mixture is incubated for 15 minutes at room temperature.
90 µL of serum-free DMEM are then added and the final mixture is transferred onto the culture cells. The cells are then incubated in a CO2 incubator. The efficacy of the transport is measured at 5 h by flow cytometry.

Figure 11A:
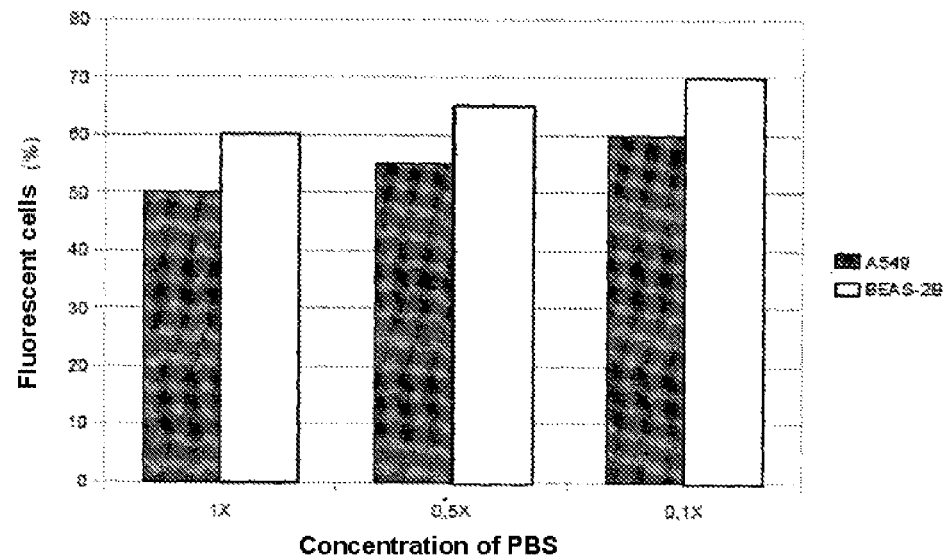
FIGS. 11a and 11b show the influence of the ionic force of the medium on the efficacy of the transport (11a) and on the quantity of antibodies transported (11b) into the A549 and BEAS-2B cells.
Figure 11B:
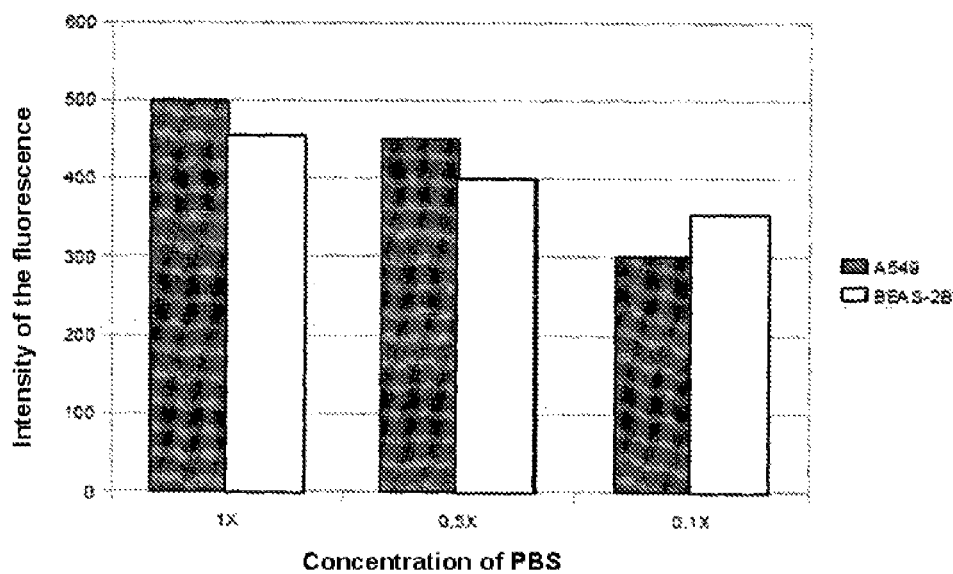

The results presented in FIGS. 11a and 11b show that the ionic force of the medium in which the mixture of the formulation prepared according to example 2.2a with the antibody is performed influences the way in which the antibody is transported into the cells. The following tendency is clear from the results obtained:

The weaker the ionic force of the medium is (PBS 0.5× and PBS 0.1×), the higher the percentage of cells having internalized the antibody is. However, the quantity of antibodies present in each cell is inversely proportional to this.

i) Effect of the Quantity of Antibodies on the Efficacy of the Transport

Figure 12:
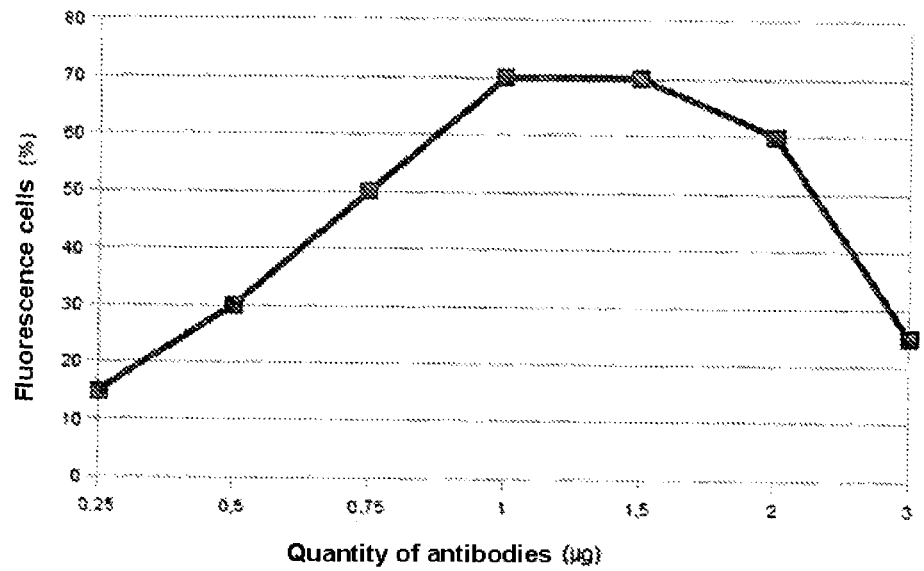
FIG. 12 shows the influence of the quantity of antibodies on the efficacy of the transport into NIH3T3 cells.

NIH3T3 cells are seeded in a 24-well plate (100,000 cells/well) and cultivated in 500 µL of DMEM in the presence of serum in a CO2 incubator for 24 hours. The transport of antibodies is performed as described in example 2.2b. The efficacy of the transport is measured at 5 h by flow cytofluorometry. The results presented in FIG. 12 show that there is an optimal quantity of antibodies necessary for the same formulation volume prepared according to example 2.2a.

j) Translocation of the NFkb-p50 Protein Viewed, by Means of an Antibody

A549 cells are seeded in a 24-well plate (100,000 cells/well) and cultivated in 500 µL of DMEM in the presence of serum in a CO2 incubator for 24 hours.

The transport of antibodies is then performed as follows:
1 µg of p50 human anti-NFkB mouse IgG (containing 1% bovine serum albumin or BSA) labeled with Alexa Fluor 488 is diluted in 10 µL of PBS buffer.
2 µL of formulation prepared according to example 2.2a are added and the mixture is incubated for 15 minutes at room temperature.
90 µL of serum-free DMEM are then added and the final mixture is transferred onto the NIH3T3 cells in culture.

The cells are then incubated in a CO2 incubator for 4 h. The cells are then treated with phorbol 12-myristate 13-acetate at 75 ng/mL for 3 h. The efficacy of the transport of NFkB p50 is viewed under fluorescence microscopy after the cells have been fixed by a formalin solution.

Figure 13:
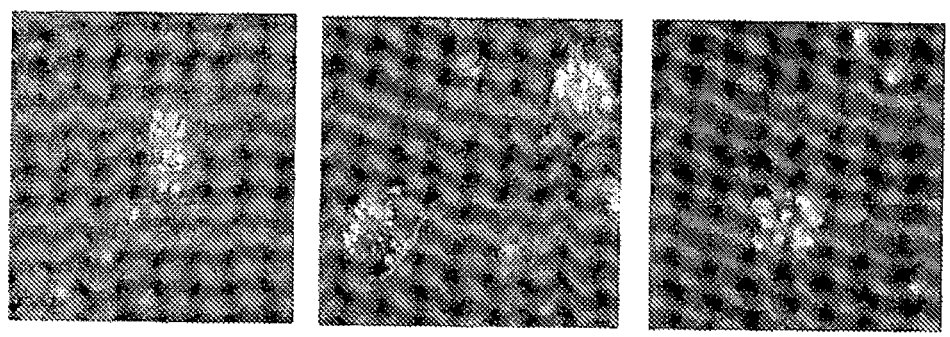
FIG. 13 shows, in three different images, the transport of an anti-NFkB p50 antibody into A549 cells.

The results presented in FIG. 13 show a nuclear localization of the NFkBp50 protein.

The labeling is relatively punctiform, which shows the accumulation of the protein in certain areas of the nucleus under the effect of the phorbol ester.

k) Use of the Compound in In Vivo Applications

50 µg of IgG from DightLight 488-labeled goat serum are diluted in 400 µL of a solution containing 5% glucose.

6 µL of the formulation prepared according to example 2.2a concentrated ten times are added and the mixture is incubated for 20 minutes at room temperature.

The mixture is then injected into the vein of the tail of an adult mouse. The mouse is sacrificed 2 days later, the tail is removed, ground, homogenized and centrifuged in order to enable the assay of the antibody still present by means of a fluorometer.

Figure 14:
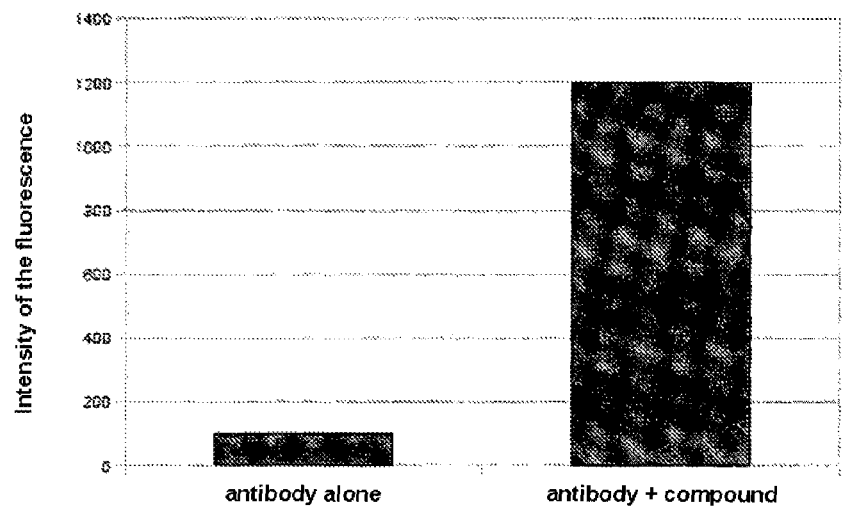
FIG. 14 shows the transport of an antibody in the mouse.

The results presented in FIG. 14 clearly show the immunotherapeutic potential of the formulation prepared according to example 2.2a because it is capable of transporting the antibody into the mouse tail, while no fluorescent activity is observed in the absence of a formulation prepared according to example 2.2a.

l) Biological Activity of an Antibody, Directed Against an Oncoprotein, Associated with One of the Compounds Prepared as Described Above U87 and 3T6 cells are seeded in a 24-well plate (75,000 cells/well) and cultivated in 500 µL of DMEM containing 10% serum in a CO2 incubator for 16 h. 1 or 2 µg of a monoclonal mouse antibody directed against and intracellular oncoprotein (antitumor antibody) or 1 or 2 µg of a goat serum IgG (control antibody) are transported into the cells according to the protocol described in example 2.2e.

After 48 h of incubation in a CO2 incubator at 37° C., the cells are washed with PBS, then separated in a trypsin solution before being counted.

Figure 15A:
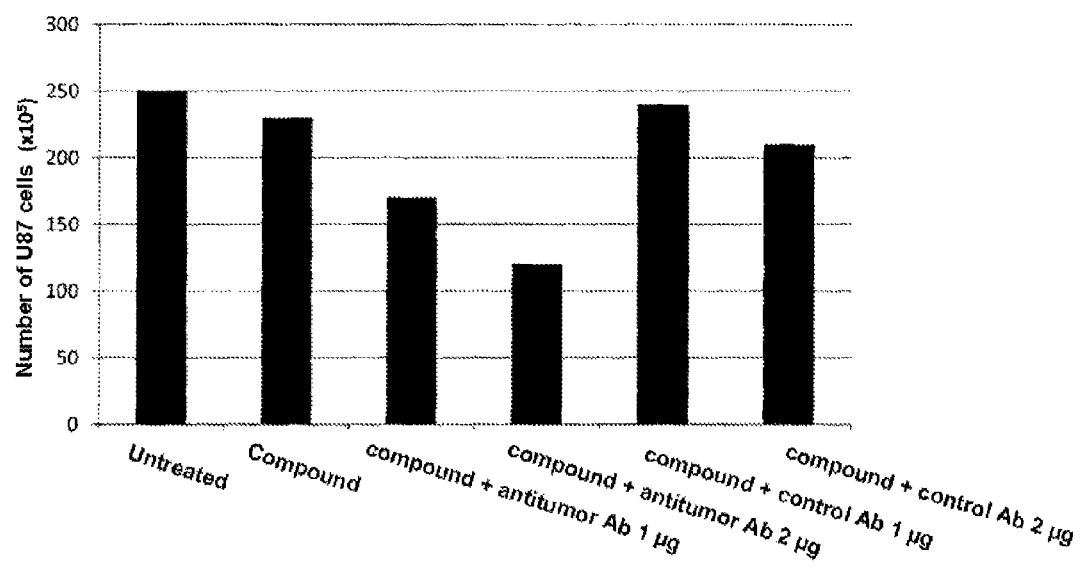
FIGS. 15a and 15b show that it is possible to inhibit the growth of tumor cells using compounds complexed to an antibody directed against an intracellular protein involved in cell proliferation and oncogenesis.
Figure 15B:
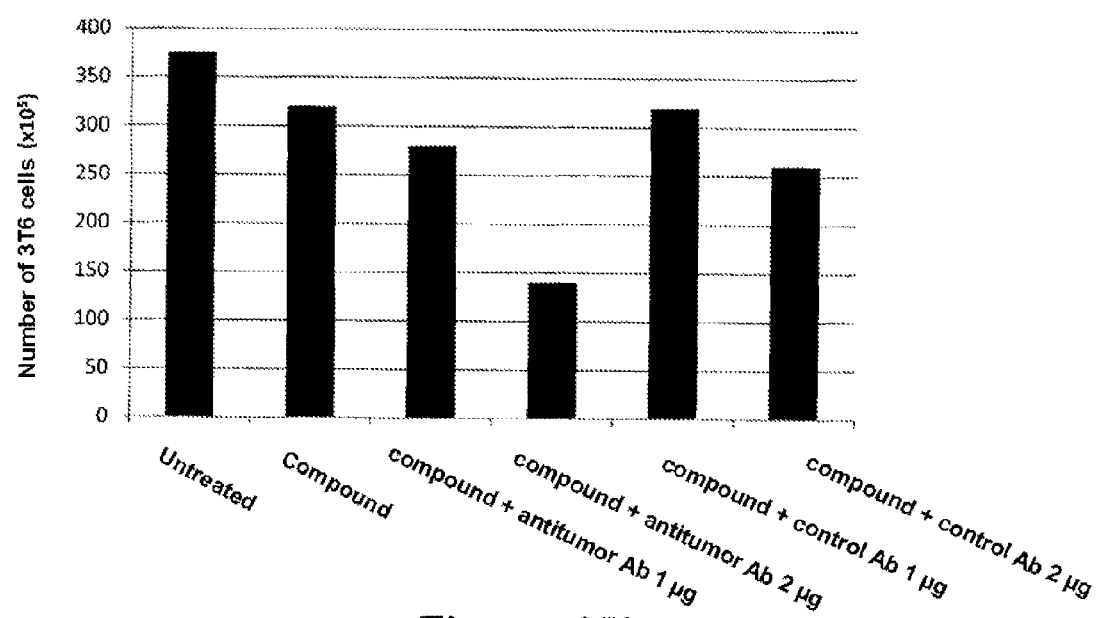

The results presented in FIGS. 15a and 15b show that it is possible to specifically inhibit the cell proliferation by means of a monoclonal antibody directed against an oncoprotein and transported into the cell by a compound synthesized as described in example 1.

The invention claimed is:
1. A compound of formula (I):

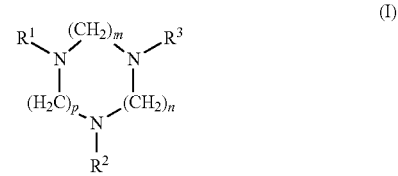

(I)

wherein:
$R^1$ has formula (V):

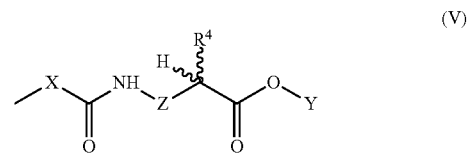

(V)

wherein:
X represents an alkylene group and selected from $C_1$-$C_4$ alkylene groups;
Y represents a linear, saturated or unsaturated alkyl chain selected from $C_{12}$-$C_{18}$ alkyl chains;
Z represents a covalent bond and $R^4$ represents a hydrogen atom, the side chain of an amino acid, or a group of formula (VI):

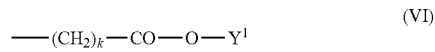

(VI)

wherein k is 1 or 2, and $Y^1$ represents a linear, saturated or unsaturated alkyl chain selected from $C_{12}$-$C_{18}$ alkyl chains,
$R^2$ represents a hydrogen atom or a linear, branched and/or cyclic, saturated or unsaturated hydrocarbon group selected from groups having 1 to 20 carbon atoms, wherein the hydrocarbon group also includes at least one of a carboxyl group and an amine group covalently bound to a chain of the hydrocarbon group, and wherein the hydrocarbon group has at least one functional cationic group chosen from amino group, guanidino group, imidazole chain-containing group, and quaternary ammonium-containing group;
$R^3$ represents a hydrogen atom or is identical to R', or is identical to $R^2$,
and
m, n and p are equal to 2.

2. The compound according to claim 1, which is selected from the group consisting of:
1,4-didodecyl-N(7'-carboxymethyl-1',4',7'-triazacyclononane)-L-aspartate;
1,5-didodecyl-N(7'-carboxymethyl-1',4',7'-triazacyclononane)-L-glutamate;
1,4-ditetradecyl-N(7'-carboxymethyl-1',4',7'-triazacyclononane)-L-aspartate;
1,5-ditetradecyl-N(7'-carboxymethyl-1',4',7'-triazacyclononane)-L-glutamate;
1,4-dihexadecyl-N(7'-carboxymethyl-1',4',7'-triazacyclononane)-L-aspartate;
1,5-dihexadecyl-N(7'-carboxymethyl-1',4',7'-triazacyclononane)-L-glutamate;
1,4-dioctadecyl-N(7'-carboxymethyl-1',4',7'-triazacyclononane)-L-aspartate;
1,5-dioctadecyl-N(7'-carboxymethyl-1',4',7'-triazacyclononane)-L-glutamate;
1,4-dioleyl-N(7'-carboxymethyl-1',4',7'-triazacyclononane)-L-aspartate;
1,5-dioleyl-N(7'-carboxymethyl-1',4',7'-triazacyclononane)-L-glutamate;
1,4-dioleyl-N(1',4'-dibetainyl-7'-carboxymethyl-1',4',7'-triazacyclononane)-L-aspartate;
1,5-dioleyl-N(1',4'-dibetainyl-7'-carboxymethyl-1',4',7'-triazacyclononane)-L-glutamate;
1,4-dioleyl-N(1',4'-diornithyl-7'-carboxymethyl-1',4',7'-triazacyclononane)-L-aspartate;
1,5-dioleyl-N(1',4'-diornithyl-7'-carboxymethyl-1',4',7'-triazacyclononane)-L-glutamate;
-1,4-dioleyl-N(1',4'-diarginyl-7'-carboxymethyl-1',4',7'-tri azacyclononane)-L-aspartate;
1,5-dioleyl-N(1',4'-diarginyl-7'-carboxymethyl-1',4',7'-triazacyclononane)-L-glutamate;
1-octadecyl, 4-oleyl-N(7'-carboxymethyl-1',4',7'-triazacyclononane)-L-aspartate.

3. A pharmaceutical composition including:
an active molecule adapted for administration to a human or animal to establish a medical diagnosis or restore, correct or modify a physiological function by exerting a pharmacological, immunological or metabolic action, wherein the active molecule is selected from the group consisting of proteins, antibodies, nucleic acids and antitumor agents;
the compound according to claim 1; and
a pharmaceutically acceptable carrier.

4. The compound 1,5-dioleyl-N(7'-carboxymethyl-1',4',7'-triazacyclononane)-L-glutamate.

5. The compound according to claim 1, which is selected from the group consisting of:
1,4-didodecyl-N(7'-carboxymethyl-1',4',7'-triazacyclononane)-L-aspartate;
1,4-ditetradecyl-N(7'-carboxymethyl-1',4',7'-triazacyclononane)-L-aspartate;
1,4-dihexadecyl-N(7'-carboxymethyl-1',4',7'-triazacyclononane)-L-aspartate;
1,4-dioctadecyl-N(7'-carboxymethyl-1',4',7'-triazacyclononane)-L-aspartate;
1,4-dioleyl-N(7'-carboxymethyl-1',4',7'-triazacyclononane)-L-aspartate;
1,4-dioleyl-N(1',4'-dibetainyl-7'-carboxymethyl-1',4',7'-triazacyclononane)-L-aspartate;
1,4-dioleyl-N(1',4'-diornithyl-7'-carboxymethyl-1',4',7'-triazacyclononane)-L-aspartate;
1,4-dioleyl-N(1',4'-diarginyl-7'-carboxymethyl-1',4',7'-triazacyclononane)-L-aspartate;
1-octadecyl, 4-oleyl-N(7'-carboxymethyl-1',4',7'-triazacyclononane)-L-aspartate.

6. The compound according to claim 1, which is selected from the group consisting of:
1,5-didodecyl-N(7'-carboxymethyl-1',4',7'-triazacyclononane)-L-glutamate;
1,5-ditetradecyl-(7'-carboxymethyl-1',4',7'-triazacyclononane)-L-glutamate;
1,5-dihexadecyl-N(7'-carboxymethyl-1',4',7'-triazacyclononane)-L-glutamate;
1,5-dioctadecyl-N(7'-carboxymethyl-1',4',7'-triazacyclononane)-L-glutamate;
1,5-dioleyl-N(7'-carboxymethyl-1',4',7'-triazacyclononane)-L-glutamate;
1,5-dioleyl-N(1',4'-dibetainyl-7'-carboxymethyl-1',4',7'-triazacyclononane)-L-glutamate;
1,5-dioleyl-N(1',4'-diornithyl-7'-carboxymethyl-1',4',7'-triazacyclononane)-L-glutamate;
1,5-dioleyl-N(1',4'-diarginyl-7'-carboxymethyl-1',4',7'-triazacyclononane)-L-glutamate.

7. The pharmaceutical composition according to claim 3, further comprising a colipid, wherein the colipid is dioleoylphosphatidylethanolamine.

* * * * *